US009107824B2

(12) United States Patent
Pilkiewicz et al.

(10) Patent No.: US 9,107,824 B2
(45) Date of Patent: Aug. 18, 2015

(54) METHODS OF TREATING CANCER WITH HIGH POTENCY LIPID-BASED PLATINUM COMPOUND FORMULATIONS ADMINISTERED INTRAPERITONEALLY

(75) Inventors: Frank G. Pilkiewicz, Princeton Junction, NJ (US); Roman Perez-Soler, New York, NY (US); Yiyu Zou, Bronx, NY (US); Walter R. Perkins, Pennington, NJ (US); Jin K. Lee, Belle Mead, NJ (US); Vladimir Malinin, Plainsboro, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 1194 days.

(21) Appl. No.: 12/122,191

(22) Filed: May 16, 2008
(Under 37 CFR 1.47)

(65) Prior Publication Data

US 2009/0130193 A1 May 21, 2009

Related U.S. Application Data

(63) Continuation-in-part of application No. 11/592,754, filed on Nov. 3, 2006, now abandoned.

(60) Provisional application No. 60/734,474, filed on Nov. 8, 2005.

(51) Int. Cl.
*A61K 9/127* (2006.01)
*A61K 9/16* (2006.01)
*A61K 9/00* (2006.01)
(Continued)

(52) U.S. Cl.
CPC .............. *A61K 9/127* (2013.01); *A61K 9/0019* (2013.01); *A61K 9/1617* (2013.01); *A61K 31/282* (2013.01); *A61K 31/555* (2013.01); *A61K 33/24* (2013.01)

(58) Field of Classification Search
None
See application file for complete search history.

(56) References Cited

U.S. PATENT DOCUMENTS 3,993,754 A 11/1976 Rahman et al.
4,105,027 A 8/1978 Lundquist
(Continued)

FOREIGN PATENT DOCUMENTS

CN 1088777 7/1994
EP 0551169 7/1993
(Continued)

OTHER PUBLICATIONS

Office Action for Australian Application No. 2003302314, dated May 26, 2008, 2 pages.
(Continued)

*Primary Examiner* — Bethany Barham
*Assistant Examiner* — Barbara Frazier
(74) *Attorney, Agent, or Firm* — Cooley LLP

(57) ABSTRACT

One aspect of the invention relates to methods of treating cancer in a patient comprising administering intraperitoneally to a patient in need thereof a cancer treating effective amount of a composition comprising a lipid-complexed platinum compound wherein the concentration of the platinum compound of the lipid-complexed platinum compound composition is greater than about 1.2 mg/ml. Another aspect of the invention relates to lipid-complexed platinum compound compositions where the concentration of the platinum compound is greater than about 1.2 mg/ml.

31 Claims, 11 Drawing Sheets

(51) Int. Cl.
*A61K 31/282* (2006.01)
*A61K 31/555* (2006.01)
*A61K 33/24* (2006.01)

(56) References Cited

U.S. PATENT DOCUMENTS

| | | | |
|---|---|---|---|
| 4,145,410 A | 3/1979 | Sears | |
| 4,192,309 A | 3/1980 | Poulsen | |
| 4,224,179 A | 9/1980 | Schneider | |
| 4,227,522 A | 10/1980 | Carris | |
| 4,235,871 A | 11/1980 | Papahadjopoulos et al. | |
| 4,451,447 A | 5/1984 | Kaplan et al. | |
| 4,522,803 A | 6/1985 | Lenk et al. | |
| 4,529,561 A | 7/1985 | Hunt et al. | |
| 4,572,425 A | 2/1986 | Russell | |
| 4,588,578 A | 5/1986 | Fountain et al. | |
| 4,590,001 A | 5/1986 | Stjernholm | |
| 4,627,432 A | 12/1986 | Newell et al. | |
| 4,721,612 A | 1/1988 | Janoff et al. | |
| 4,767,874 A | 8/1988 | Shima et al. | |
| 4,778,054 A | 10/1988 | Newell et al. | |
| 4,811,731 A | 3/1989 | Newell et al. | |
| RE33,071 E | 9/1989 | Stjernholm | |
| 4,889,724 A | 12/1989 | Kasan et al. | |
| 4,975,282 A | 12/1990 | Cullis et al. | |
| 4,981,692 A | 1/1991 | Popescu et al. | |
| 5,008,050 A | 4/1991 | Cullis et al. | |
| 5,013,556 A | 5/1991 | Woodle et al. | |
| 5,019,369 A | 5/1991 | Presant et al. | |
| 5,030,453 A | 7/1991 | Lenk et al. | |
| 5,035,237 A | 7/1991 | Newell et al. | |
| 5,049,388 A | 9/1991 | Knight et al. | |
| 5,059,421 A | 10/1991 | Loughrey et al. | |
| 5,077,056 A | 12/1991 | Bally et al. | |
| 5,077,057 A | 12/1991 | Szoka, Jr. | |
| 5,094,854 A | 3/1992 | Ogawa et al. | |
| 5,117,022 A | 5/1992 | Khokhar et al. | |
| 5,141,751 A | 8/1992 | Tomikawa et al. | |
| 5,169,637 A | 12/1992 | Lenk et al. | |
| 5,186,940 A | 2/1993 | Khokhar et al. | |
| 5,225,212 A | 7/1993 | Martin et al. | |
| 5,264,221 A | 11/1993 | Tagawa et al. | |
| 5,320,906 A * | 6/1994 | Eley et al. | 428/402.2 |
| 5,567,434 A | 10/1996 | Szoka, Jr. | |
| 5,616,334 A | 4/1997 | Janoff et al. | |
| 5,641,662 A | 6/1997 | Debs et al. | |
| 5,665,383 A | 9/1997 | Grinstaff et al. | |
| 5,756,353 A | 5/1998 | Debs | |
| 5,780,054 A | 7/1998 | Tardi et al. | |
| 5,795,589 A | 8/1998 | Mayer et al. | |
| 5,945,122 A * | 8/1999 | Abra et al. | 424/450 |
| 5,997,899 A | 12/1999 | Ye et al. | |
| 6,090,407 A | 7/2000 | Knight et al. | |
| 6,126,966 A | 10/2000 | Abra et al. | |
| 6,147,060 A | 11/2000 | Zasloff et al. | |
| 6,211,388 B1 | 4/2001 | Tsuji et al. | |
| 6,221,388 B1 | 4/2001 | Hersch et al. | |
| 6,274,115 B1 | 8/2001 | Presant et al. | |
| 6,352,996 B1 | 3/2002 | Cao et al. | |
| 6,419,901 B2 | 7/2002 | Placke et al. | |
| 6,440,393 B1 | 8/2002 | Waldrep et al. | |
| 6,451,784 B1 | 9/2002 | Placke et al. | |
| 6,511,676 B1 * | 1/2003 | Boulikas | 424/450 |
| 6,599,912 B1 | 7/2003 | Au et al. | |
| 6,669,958 B1 | 12/2003 | Trager et al. | |
| 6,723,338 B1 | 4/2004 | Sarris et al. | |
| 6,726,925 B1 | 4/2004 | Needham | |
| 6,787,132 B1 | 9/2004 | Gabizon et al. | |
| 6,793,912 B2 | 9/2004 | Pilkiewicz et al. | |
| 6,852,334 B1 | 2/2005 | Cullis et al. | |
| 6,921,527 B2 | 7/2005 | Platz et al. | |
| 7,025,988 B2 | 4/2006 | Zadi | |
| 7,063,860 B2 | 6/2006 | Chancellor et al. | |
| 7,544,369 B2 | 6/2009 | Boni et al. | |
| 2001/0010822 A1 | 8/2001 | Cherian | |
| 2002/0009415 A1 | 1/2002 | Batich et al. | |
| 2002/0012998 A1 | 1/2002 | Gonda et al. | |
| 2002/0110586 A1 | 8/2002 | Madden et al. | |
| 2002/0182248 A1 | 12/2002 | Yamauchi et al. | |
| 2002/0187105 A1 | 12/2002 | Zou et al. | |
| 2003/0017210 A1 | 1/2003 | Debregeas et al. | |
| 2003/0059375 A1 | 3/2003 | Perez-Soler et al. | |
| 2003/0059402 A1 | 3/2003 | Jin et al. | |
| 2003/0099718 A1 | 5/2003 | Burrell et al. | |
| 2003/0185879 A1 | 10/2003 | Boulikas | |
| 2003/0224039 A1 | 12/2003 | Boni et al. | |
| 2004/0022842 A1 | 2/2004 | Eriguchi et al. | |
| 2004/0101553 A1 | 5/2004 | Lee et al. | |
| 2004/0156888 A1 | 8/2004 | Jensen et al. | |
| 2004/0170678 A1 * | 9/2004 | Madden et al. | 424/450 |
| 2005/0037341 A1 | 2/2005 | Dierynck et al. | |
| 2005/0074499 A1 | 4/2005 | Tagawa et al. | |
| 2005/0107287 A1 | 5/2005 | Pilkiewicz et al. | |
| 2005/0207987 A1 | 9/2005 | Speirs et al. | |
| 2005/0238705 A1 | 10/2005 | Hu et al. | |
| 2005/0249822 A1 | 11/2005 | Pilkiewicz et al. | |
| 2006/0159712 A1 | 7/2006 | Lee et al. | |
| 2006/0246124 A1 | 11/2006 | Pilkiewicz et al. | |
| 2007/0065522 A1 | 3/2007 | Pilkiewicz et al. | |
| 2007/0122350 A1 | 5/2007 | Pilkiewicz et al. | |
| 2007/0190182 A1 | 8/2007 | Pilkiewicz et al. | |
| 2008/0187578 A1 | 8/2008 | Lee et al. | |
| 2009/0202431 A1 | 8/2009 | Gibbs et al. | |
| 2014/0065205 A1 | 3/2014 | Anthony et al. | |

FOREIGN PATENT DOCUMENTS

| | | |
|---|---|---|
| EP | 0719546 | 7/1996 |
| EP | 1369132 | 12/2003 |
| JP | H05-255070 | 10/1993 |
| JP | 2001-501173 | 1/2001 |
| JP | 2003-277272 | 10/2003 |
| JP | 2004-010481 | 1/2004 |
| WO | WO 85/00968 | 3/1985 |
| WO | WO 86/01102 | 2/1986 |
| WO | WO 87/02219 | 4/1987 |
| WO | WO 89/00846 | 2/1989 |
| WO | WO 91/16038 | 10/1991 |
| WO | WO 95/28948 | 11/1995 |
| WO | WO 98/07409 | 2/1998 |
| WO | WO 98/24425 | 6/1998 |
| WO | WO 98/29110 | 7/1998 |
| WO | WO 98/33481 | 8/1998 |
| WO | WO 99/15153 | 4/1999 |
| WO | WO 00/27359 | 5/2000 |
| WO | WO 01/32139 | 5/2001 |
| WO | WO 01/34130 | 5/2001 |
| WO | WO 01/82892 | 11/2001 |
| WO | WO 03/015521 | 2/2003 |
| WO | WO 03/015707 | 2/2003 |
| WO | WO 2004/047802 | 6/2004 |
| WO | WO 2004/054499 | 7/2004 |
| WO | WO 2005/037341 | 4/2005 |
| WO | WO 2005/089448 | 9/2005 |
| WO | WO 2005/112957 | 12/2005 |
| WO | WO 2006/055352 | 5/2006 |
| WO | WO 2007/056264 | 5/2007 |
| WO | WO 2007/099377 | 9/2007 |
| WO | WO 2009/100330 | 8/2009 |
| WO | WO 2011/103591 | 8/2011 |
| WO | WO 2014/039533 | 3/2014 |

OTHER PUBLICATIONS

First Office Action for Chinese Application No. 03821989.1, dated Feb. 23, 2007, 4 pages.
Second Office Action for Chinese Application No. 03821989.1, dated Jun. 14, 2008, 6 pages.
Supplementary European Search Report for European Application No. 03810869.2, mailed Jul. 24, 2007, 3 pages.
Office Action for Israeli Application No. 166654, dated Aug. 7, 2008, 1 page.
Office Action for Indian Patent Application 301/CHENP/2005, dated Mar. 7, 2006, 3 pages.

(56) References Cited

OTHER PUBLICATIONS

Office Action for Japanese Application No. 2004-560279, dated Nov. 6, 2009, 3 pages.
Office Action for New Zealand Application No. 538179, dated Aug. 29, 2006, 1 page.
Office Action for New Zealand Application No. 538179, dated Mar. 5, 2008, 2 pages.
Office Action for U.S. Appl. No. 10/634,144, mailed Oct. 29, 2008, 9 pages.
Office Action for U.S. Appl. No. 10/634,144, mailed Jul. 27, 2007, 7 pages.
Office Action for U.S. Appl. No. 10/634,144, mailed Jun. 24, 2009, 8 pages.
Office Action for U.S. Appl. No. 10/634,144, mailed Mar. 28, 2008, 8 pages.
International Search Report for International Application No. PCT/US2003/024350, mailed Aug. 26, 2004, 1 page.
Supplementary European Search Report for European Application No. 09708680.5, mailed Apr. 4, 2013, 5 pages.
Office Action for U.S. Appl. No. 12/027,752, mailed Dec. 15, 2014, 11 pages.
Office Action for U.S. Appl. No. 12/027,752, mailed Apr. 30, 2013, 7 pages.
Office Action for U.S. Appl. No. 12/027,752, mailed Jan. 29, 2010, 12 pages.
Office Action for U.S. Appl. No. 12/027,752, mailed Nov. 8, 2013, 10 pages.
Office Action for U.S. Appl. No. 12/027,752, mailed Oct. 12, 2010, 12 pages.
International Search Report and Written Opinion for International Application No. PCT/US2009/033389, mailed Aug. 17, 2009, 8 pages.
Office Action for Chinese Application No. 200580038178.4, issued May 8, 2009, 13 pages.
Supplementary European Search Report for European Application No. 05851444.9, mailed Dec. 9, 2009, 8 pages.
Office Action for Indian Patent Application 3651/DELNP/2007, dated Nov. 12, 2012, 2 pages.
Notification of Reasons for Refusal for Japanese Application No. 2007-540183, issued Dec. 13, 2011, 2 pages.
Decision of Refusal for Japanese Application No. 2007-540183, issued Oct. 16, 2012, 2 pages.
Notification of Reasons for Refusal for Japanese Application No. 2007-540183, issued Jun. 12, 2012, 2 pages.
Office Action for New Zealand Application No. 555360, dated Aug. 7, 2008, 2 pages.
Office Action for U.S. Appl. No. 11/269,163, mailed Apr. 9, 2010, 23 pages.
Office Action for U.S. Appl. No. 11/269,163, mailed Oct. 14, 2009, 18 pages.
International Search Report and Written Opinion for International Application No. PCT/US2005/040489, mailed Jun. 13, 2006, 5 pages.
Office Action for U.S. Appl. No. 11/592,754, mailed Jul. 17, 2009, 23 pages.
Office Action for U.S. Appl. No. 11/592,754, mailed Apr. 28, 2008, 20 pages.
Office Action for U.S. Appl. No. 11/592,754, mailed Apr. 7, 2010, 17 pages.
Office Action for U.S. Appl. No. 11/592,754, mailed Feb. 10, 2009, 20 pages.
International Search Report and Written Opinion for International Application No. PCT/US2006/043159, mailed May 8, 2007, 5 pages.
Office Action for Australian Application No. 2002323266, dated Oct. 30, 2006, 1 page.
Supplementary European Search Report for European Application No. 02757236.1, mailed Feb. 29, 2008, 3 pages.
Notice of Reasons for Rejection for Japanese Application No. 2003-520668, mailed Nov. 4, 2008, 6 pages.
Office Action for U.S. Appl. No. 10/224,293, mailed Jun. 3, 2009, 13 pages.
Office Action for U.S. Appl. No. 10/224,293, mailed Jan. 14, 2008, 24 pages.
Office Action for U.S. Appl. No. 10/224,293, mailed Jun. 28, 2006, 21 pages.
Office Action for U.S. Appl. No. 10/224,293, mailed Feb. 22, 2005, 10 pages.
Office Action for U.S. Appl. No. 10/224,293, mailed Sep. 26, 2008, 15 pages.
Office Action for U.S. Appl. No. 10/224,293, mailed May 14, 2007, 19 pages.
Office Action for U.S. Appl. No. 10/224,293, mailed Oct. 7, 2005, 16 pages.
Office Action for U.S. Appl. No. 10/224,293, mailed Aug. 26, 2004, 9 pages.
International Search Report for International Application No. PCT/US2002/026408, mailed Aug. 14, 2003, 2 pages.
Supplementary European Search Report for European Application No. 02757235.3, mailed Feb. 29, 2008, 3 pages.
Office Action for U.S. Appl. No. 10/224,532, mailed Nov. 20, 2003, 9 pages.
International Search Report for International Application No. PCT/US2002/026407, mailed Oct. 16, 2002, 2 pages.
International Preliminary Examination Report for International Application No. PCT/US2002/026407, dated Jun. 27, 2003, 3 pages.
Office Action for U.S. Appl. No. 10/945,527, mailed Nov. 30, 2007, 10 pages.
Office Action for U.S. Appl. No. 10/945,527, mailed Apr. 17, 2007, 23 pages.
Office Action for U.S. Appl. No. 10/945,527, mailed Aug. 25, 2006, 20 pages.
International Search Report for International Application No. PCT/US2013/058025, mailed Jan. 10, 2014, 2 pages.
Alberts, D. S. et al., "Intraperitoneal cisplatin plus intravenous cyclophosphamide versus intravenous cisplatin plus intravenous cyclophosphamide for stage III ovarian cancer," New England Journal of Medicine, 335(26):1950-1955 (1996).
Alderden, R. A. et al., "The discovery and development of cisplatin," Journal of Chemical Education, 83(5):728-734 (2006).
Allen, T. M. et al., "Liposomal drug delivery systems: From concept to clinical applications," Advanced Drug Delivery Reviews, 65:36-48 (2013).
Allison, D. C. et al., "A Meta-Analysis of Osteosarcoma Outcomes in the Modern Medical Era," Sarcoma, vol. 2012, Article ID 704872 (2012), 10 pages.
Ando, K. et al., "Current Therapeutic Strategies and Novel Approaches in Osteosarcoma," Cancers, 5:591-616 (2013).
Bacci, G. et al., "Osteogenic Sarcoma of the Extremity with Detectable Lung Metastases at Presentation. Results of Treatment of 23 Patients with Chemotherapy followed by Simultaneous Resection of Primary and Metastatic Lesions." Cancer, 79(2):245-254 (1997).
Bacci, G. et al., "Treatment and outcome of recurrent osteosarcoma: Experience at Rizzoli in 235 patients initially treated with neoadjuvant chemotherapy," Acta Oncologia, 44:748-755 (2005).
Bally, M. B. et al., "Novel procedures for generating and loading liposomal systems," In: Liposomes as Drug Carriers, Gregoriadis, G. (ed.), John Wiley & Sons Ltd., 13 pages (1988).
Bangham, A. D. et al., "Diffusion of Univalent Ions across the Lamellae of Swollen Phospholipids," J. Mol. Biol., 13:238-252 (1965).
Banno, B. et al., "The functional roles of poly(ethylene glycol)-lipid and lysolipid in the drug retention and release from lysolipid-containing thermosensitive liposomes in vitro and in vivo," Journal of Pharmaceutical Science, 99(5):2295-2308 (2010).
Barnham, K. J. et al., "Ring-Opened Adducts of the Anticancer Drug Carboplatin with Sulfur Amino Acids," Inorg. Chem., 35(4):1065-1072 (1996).
Bates, S. R. et al., "Phospholipids co-isolated with rat surfactant protein C account for the apparent protein-enhanced uptake of liposomes into lung granular pneumocytes," Exp. Lung Res., 15(5):695-708 (1989).

(56) References Cited

OTHER PUBLICATIONS

Baum, E. S. et al., "Phase II trial of cisplatin in refractory childhood cancer: Children's cancer study group report," Cancer Treat. Rep., 65:815-822 (1981).
Bell, J. H. et al., "Dry powder aerosols I: A new powder inhalation device," J. Pharm. Sci., 60(10):1559-1564 (1971).
Bellmann, R. et al., "Differences in pharmacokinetics of amphotericin B lipid formulations despite clinical equivalence," Clinical Infection Diseases, 36:1500-1501 (2003).
Berek, J. S. et al., "Intraperitoneal administration of biologic agents," Int. J. Gynecol. Cancer, 1:26-29 (1992).
Bielack, S. S. et al., "Second and Subsequent Recurrences of Osteosarcoma: Presentation, Treatment, and Outcomes of 249 Consecutive Cooperative Osteosarcoma Study Group Patients," Journal of Clinical Oncology, 27(4):557-565 (2009).
Bielack, S. et al., "Osteosarcoma: ESMO Clinical Recommendations for diagnosis, treatment and follow-up," Annals of Oncology, 20(4):iv137-iv139 (2009).
Borch, R. F. et al., "Inhibition of cis-platinum nephrotoxicity by diethyldithiocarbamate rescue in a rat model," Proc. Natl. Acad. Sci USA, 76(12):6611-6614 (1979).
Boulikas, T., "Low toxicity and anticancer activity of a novel liposomal cisplatin (Lipoplatin) in mouse xenografts," Oncology Reports, 12(1):3-12 (2004).
Breathnach, O. S. et al., "Clinical Features of Patients with Stage IIIB and IV Bronchioloalelar Carcinoma of the Lung," Cancer, 86(7):1165-1173 (1999).
Briccoli, A. et al., "Resection of Recurrent Pulmonary Metastases in Patients with Osteosarcoma," Cancer, 104:1721-1725 (2005).
Brock, P. R. et al., "Cisplatin ototoxicity in children: A practical grading system," Med. Pediatr. Oncol., 19(4):295-300 (1991).
Burger, K. N. J. et al., "Nanocapsules: lipid-coated aggregates of cisplatin with high cytotoxicity," Nature Medicine, 8(1):81-84 (2002).
Cascales, L., "A study by molecular dynamics simulation of the effect of the ionic strength on the properties of a model DPPC/DPPS asymmetric membrane," The Journal of the Argentine Chemical Society, 94(1/3):157-168 (2006).
Chang, H-J et al., "Clinical development of liposome-based drugs: formulation, characterization, and therapeutic efficacy," International Journal of Nanomedicine, 7:49-60 (2012).
Chapman, D. et al., "Physicochemical Properties of Phospholipids and Lipid-Water Systems," Chapter 1 In: Liposome Technology, vol. I, Preparation of Liposomes, Gregoriadis, G. (ed.), CPC Press, Inc., Boca Raton, Florida, 21 pages (1968).
Chi, K. H. et al., "Elimination of dose limiting toxicities of cisplatin, 5-fluorouracil, and leucovorin using a weekly 24-hour infusion schedule for the treatment of patients with nasopharyngeal carcinoma," Cancer, 76(11):2186-2192 (1995).
Chiu, S. W. et al., "Structure of sphingomyelin bilayers: a simulation study," Biophysical Journal, 85:3624-3635 (2003).
Chou, A. J. et al., "Chemotherapy resistance in osteosarcoma: Current challenges and future directions," Expert Rev. Anticancer Ther., 6(7):1075-1085 (2006).
Chou, A. J. et al., "Inhaled lipid cisplatin (ILC) in the treatment of patients with relapsed/progressive osteosarcoma metastatic to the lung," Pediatr. Blood Cancer, 60:580-586 (2013).
Chou, A. J. et al., "Phase Ib/IIa study of sustained release lipid inhalation targeting cisplatin by inhalation in the treatment of patients with relapsed/progressive osteosarcoma metastic to the lung," Journal of Clinical Oncology, 2007, ACSO Annual Meeting Proceedings, 25(18S):9525 (2007).
Cisplatin Injection, Drug Information Label (Jun. 2004), 15 pages.
Cohen, G. L. et al., "Sequence dependent binding of cis-dichlorodiammineplatinum(II) to DNA," J. Am. Chem. Soc., 102(7):2487-2488 (1980).
Comis, R. L., "Carboplatin in the treatment of non-small cell lung cancer: A review," Oncology, 50(2):37-41 (1993).
Coventry, M. B. et al., "Osteogenic sarcoma," Journal of Bone and Joint Surgery, 39-A(4):741-758 (1957).
Dabkowska, A. P. et al., "The effect of neutral helper lipids on the structure of cationic lipid monolayers," Journal of The Royal Society Interface, Published online Aug. 10, 2011 (http://rsif.royalsocietypublishing.org), 15 pages.
Dai, X. et al., "Review of therapeutic strategies for osteosarcoma, chondrosarcoma, and Ewing's sarcoma," Med. Sci. Moni., 17(8):RA177-RA190 (2011).
Deamer, D. W. et al., "Chapter 1—Liposome Preparation: Methods and Mechanisms," In Liposomes, Ostro, M. (ed.), Marcel Dekker, Inc., New York, 27 pages (1983).
DeConti, R. C. et al., "Clinical and pharmacological studies with cis-Diamminedichloroplatinum(II)[1]," Cancer Research, 33:1310-1315 (1973).
Dedrick, R. L. et al., "Pharmacokinetic rationale for peritoneal drug administration in the treatment of ovarian cancer," Cancer Treat. Rep., 62(1):1-9 (1978).
DeMayo, F. et al., "Mesenchymal-epithelial interactions in lung development and repair: are modeling and remodeling the same process?," Am. J. Physiol. Lung Cell Mol. Physiol., 283:L510-L517 (2002).
Devarajan, P. et al., "Low renal toxicity of lipoplatin compared to cisplatin in animals," Anticancer Research, 24:2193-2200 (2004).
Dolman, R. C. et al., "Studies of the binding of a series of platinum(IV) complexes to plasma proteins," J. Inorg. Biochem., 88:260-267 (2002).
Embree, L. et al., "Chromatographic Analysis and Pharmacokinetics of Liposome-Encapsulated Doxorubicin in Non-Small-Cell Lung Cancer Patients," Journal of Pharmaceutical Sciences, 82(6):627-634 (1993).
Enneking, W. F. et al., "A System for the Surgical Staging of Musculoskeletal Sarcoma," Clin. Orthop. Relat. Res., 153:106-120 (1980).
Ferguson, W. S. et al., "Presurgical window of carboplatin and surgery and multidrug chemotherapy for the treatment of newly diagnosed metastatic or unresectable osteosarcoma: pediatric oncology group trial," J. Pediatr. Hematol. Oncol., 23(6):340-348 (2001).
Ferrari, S. et al., "Postrelapse survival in osteosarcoma of the extremities: prognostic factors for long-term survival," J. Clin. Oncol., 21(4):710-715 (2003).
Freise, J. et al., "Pharmacokinetics of liposome-encapsulated cisplatin in rats," Arch. Int. Pharmacodyn. Ther., 258(2):180-192 (1982).
Fuertes, M. A. et al., "Novel concepts in the development of platinum antitumor drugs," Curr. Med. Chem.—Anti-Cancer Agents, 2(4):539-551 (2002).
Fujita, J. et al., "Respiratory failure due to pulmonary lymphangitis carcinomatosis," Chest, 103(3):967-968 (1993).
Gately, D. P. et al., "Cellular accumulation of the anticancer agent cisplatin: A review," Br. J. Cancer, 67:1171-1176 (1993).
Geiger, K. et al., "Cellular distribution and clearance of aerosolized dipalmitoyl lecithin," J. Appl. Physiol., 39(5):759-766 (1975).
Gondal, J. A. et al., "Comparative pharmacological, toxicological and antitumoral evaluation of free and liposomeencapsulated cisplatin in rodents," Eur. J. Cancer, 29A(11):1536-1542 (1993).
Gonzalez-Rothi, R. J. et al., "Liposomes and pulmonary alveolar macrophages: functional and morphologic interactions," Exp. Lung Res., 17:687-705 (1991).
Goorin, A. M. et al., "Phase II/III trial of etoposide and high-dose ifosfamide in newly diagnosed metastatic osteosarcoma: A pediatric oncology group trial," J. Clin. Oncol., 20(2):426-433 (2002).
Gorlick, R., "Current concepts on the molecular biology of osteosarcoma," In: Pediatric and Adolescent Osteosarcoma, Jaffe, N. et al. (eds.), Cancer Treatment and Research, 152:467-478 (2010).
Gregoriadis, G., "Targeting of drugs: Implications in medicine," Lancet, 2:241-247 (1981).
Hambley, T. W., "Platinum binding to DNA: structural controls and consequences," J. Chem. Soc., Dalton Trans., 2711-2718 (2001).
Harris, M. B. et al., "Treatment of metastatic osteosarcoma at diagnosis: A pediatric oncology group study," J. Clin. Oncol., 16(11):3641-3648 (1998).
Harting, M. T. et al., "Management of osteosarcoma pulmonary metastases," Semin. Pediatr. Surg., 15(1):25-29 (2006).

(56) References Cited

OTHER PUBLICATIONS

Hayes, F. A. et al., "Tetany: A complication of cis-dichlorodiammineplatinum(II) therapy," Cancer Treatment Reports, 63(4):547-548 (1979).
Hickey, A. J. et al., "A new millennium for inhaler technology," Pharmaceutical Technology, pp. 116-125 (Jun. 1997).
Ho, C. et al., "Hydration and order in lipid bilayers," Biochemistry, 34(18):6188-6195 (1995).
Hoffman, P. C. et al., "Lung Cancer," The Lancet, 355:479-485 (2000).
Hojo, K. et al., "A case of adenocarcinoma of lung cancer with multiple brain metastasis and lymphangitis carcinomatosa responding well to chemotherapy with carboplatin, etoposide and ifosfamide," Jpn. J. Cancer Chemother., 19(14):2403-2406 (1992) (with English Summary).
Ishida, S. et al., "Uptake of the anticancer drug cisplatin mediated by the copper transporter Ctr1 in yeast and mammals," PNAS, 99(22):14298-14302 (2002).
Ivanov, A. I. et al., "Cisplatin Binding Sites on Human Albumin," J. Biol. Chem., 273:14721-14730 (1998).
Jaffe, N. et al., "Can Cure in Patients with Osteosarcoma Be Achieved Exclusively with Chemotherapy and Abrogation of Surgery?," Cancer, 95(10):2202-2210 (2002).
Jahnig, F., "Structural order of lipids and proteins in membranes: evaluation of fluorescence anisotropy data," Proc. Natl. Acad. Sci. USA, 76(12):6361-6365 (1979).
Jamieson, E. R. et al., "Structure, recognition, and processing of cisplatin-DNA adducts," Chem. Rev., 99(9):2467-2498 (1999).
Kelland, L. R., "Preclinical perspectives on platinum resistance," Drugs, 59(4):1-8 (2000).
Kelland, L., "The resurgence of platinum-based cancer chemotherapy," Nature Reviews, 7:573-584 (2007).
Kempf-Bielack, B. et al., "Osteosarcoma relapse after combined modality therapy: An analysis of unselected patients in the cooperative osteosarcoma study group (COSS)," J. Clin. Oncol., 23(3):559-568 (2005).
Kinoshita, A., "Investigation of cisplatin inhalation chemotherapy effects on mice after air passage implantation of FM3A cells," Journal of Japan Society for Cancer Therapy, 28(4):705-715 (1993).
Knight, V. et al., "Anti-Cancer Activity of 9-Nitrocamptothecin Liposome Aerosol in Mice," Transactions of the American Clinical and Climatological Association, 111:135-145 (2000).
Koshkina, N. V. et al., "9-Nitrocamptothecin Liposome Aerosol Treatment of Melanoma and Osteosarcoma Lung Metastases in Mice," Clinical Cancer Research, 6(7):2876-2880 (2000).
Lansky, S. B. et al., "The measurement of performance in childhood cancer patients," Cancer, 60(7):1651-1656 (1987).
Lee, D. S. et al., "Predicting survival in patients with advanced non-squamous non-small cell lung cancer: Validating the extent of metastasis," Cancer Res. Treat., 45(2):95-102 (2013).
Leekumjorn, S. et al., "Molecular simulation study of structural and dynamic properties of mixed DPPC/DPPE bilayers," Biophysical Journal, 90(11):3951-3965 (2006).
Lehninger, A. L. et al., Principles of Biochemistry, Worth Publishers: New York, pp. 111-114, 134-135, 137, 240-245, 247, 249-252, 254, 256-259, 262, 364-365, 392-393 (1993).
Leighl, N. B. et al., "A phase I study of pegylated liposomal doxorubicin hydrochloride (CaelyxTM) in combination with cyclophosphamide and vincristine as second-line treatment of patients with small-cell lung cancer," Clinical Lung Cancer, 5(2):107-112 (2003).
Lempers, E. L. M. et al., "Interactions of platinum amine compounds with sulfur-containing biomolecules and DNA fragments," Adv. Inorg. Chem. 37:175-217 (1991).
Leserman, L. et al., "Ligand Targeting of Liposomes," In: Liposomes—From Biophysics to Therapeutics, pp. 157-194, Ostro, M. (ed.), New York, NY, Marcel Dekker (1987).
Lewis, R. E. et al., "Comparative analysis of amphotericin B lipid complex and liposomal amphotericin B kinetics of lung accumulation and fungal clearance in a murine model of acute invasive pulmonary aspergillosis," Antimicrobial Agents and Chemotherapy, 51(4):1253-1258 (2007).
Lewis, R. E. et al., "Comparative pharmacodynamics of amphotericin B lipid complex and liposomal amphoterin B in a murine model of pulmonary mucormycosis," Antimicrobial Agents and Chemotherapy, 54(3):1298-1304 (2010).
Li, X-M et al., "Sphingomyelin interfacial behavior: The impact of changing acyl chain composition," Biophysical Journal, 78:1921-1931 (2000).
Liu, D. et al., "Application of liposomal technologies for delivery of platinum analogs in oncology," International Journal of Nanomedicine, 8:3309-3319 (2013).
Lloyd, P. et. al., "A new unit dose, breath actuated aerosol drug delivery system," In: Respiratory Drug Delivery V, Program and Proceedings, Dalby, R. N. (eds.), Interpharm Press, Buffalo Grove, IL, pp. 364-366 (1996).
Lopez-Berestein, G. et al., "Liposomal amphotericin B for the treatment of systemic fungal infections in patients with cancer: A preliminary study," J. Infect. Dis., 151(4):704-710 (1985).
Markman, M., "Intraperitoneal therapy of ovarian cancer," The Oncologist, 1:18-21 (1996).
Markman, M., "Intraperitoneal antineoplastic agents for tumors principally confined to the peritoneal cavity," Cancer Treatment Reviews, 13(4):219-242 (1986).
Markman, M., "Intraperitoneal chemotherapy," Semin. Oncol., 18(3):248-254 (1991).
Markman, M. et al., "Responses to second-line cisplatin-based intraperitoneal therapy in ovarian cancer: Influence of a prior response to intravenous cisplatin," J. Clin. Oncol., 9(10):1801-1805 (1991).
Maurer, N. et al., "Developments in liposomal drug delivery systems," Expert Opin. Biol. Ther., 1(6):923-947 (2001).
Mayer, L. D. et al. "Techniques for encapsulating bioactive agents into liposomes," Chemistry and Physics of Lipids, 40:333-345 (1986).
Merimsky, O. et al., "Palliative treatment for advanced or metastatic osteosarcoma," IMAJ, 6:34-38 (2004).
Meyers, P. A. et al., "Osteosarcoma," Pediatr. Clin. North Am., 44(4):973-989 (1997).
Meyers, P. A. et al., "Osteogenic sarcoma with clinically detectable metastasis at initial presentation," J. Clin. Oncol., 11(3):449-453 (1993).
Mills, J. K. et al., "Lysolipid incorporation in dipalmitoylphosphatidylcholine bilayer membranes enhances the ion permeability and drug release rates at the membrane phase transition," Biochimica et Biophysica Acta, 1716:77-96 (2005).
Mizumura, Y. et al., "Cisplatin-incorporated Polymeric Micelles Eliminate Nephrotoxicity, While Maintaining Antitumor Activity," Jpn. J. Cancer Res., 92:328-336 (2001).
Mohseny, A. B. et al., "Osteosarcoma originates from mesenchymal stem cells in consequence of aneuploidization and genomic loss of Cdkn2," J. Pathol., 219(3):294-305 (2009).
Needham, D. et al., "A new temperature-sensitive liposome for use with mild hyperthermia: characterization and testing in a human tumor xenograft model," Cancer Research, 60(5):1197-1201 (2000).
Nelson, D. L., Lehninger Principles of Biochemistry, 3rd Edition, Worth Publishers, pp. 364-365, 390, 392-393 (2000).
Nelson, G. J., "Composition of neutral lipids from erythrocytes of common mammals," Journal of Lipid Research, 8:374-379 (1967).
Oken, M. M. et al., Toxicity and response criteria of the Eastern Cooperative Oncology Group, Am. J. Clin. Oncol., 5:649-655 (1982).
Okuyuma, S. et al., "Reinforcing aerosol cisplatin for radiotherapy of laryngeal cancer," Tohoku Journal of Experimental Medicine, 169(3):253-255 (1993).
Pandit, S. A. et al., "Sphingomyelin-cholesterol domains in phospholipid membranes: atomistic simulation," Biophysical Journal, 87:1092-1100 (2004).
Papahadjopoulos, D. et al., "Phospholipid model membranes. I. Structural characteristics of hydrated liquid crystals," Biochimica et Biophysica Acta., 135:624-638 (1967).

(56) References Cited

OTHER PUBLICATIONS

Parry-Billings, M. et al., "Design, development and performance of a novel multidose dry-powder inhaler," Pharmaceutical Technology, pp. 24-34 (Nov. 1999) (previously appeared in Pharmaceutical Technology, 23:70-82, Oct. 1999).

Perez-Soler, R. et al., "Toxicity and antitumor activity of cis-Bis-cyclopentenecarboxylato-1,2-diaminocyclohexane Platinum(II) encapsulated in multilamellar vesicles," Cancer Research, 46(12):6269-6273 (1986).

Perkins et al., "An Inhalation Formulation of Liposomal Cisplatin (SLIPMCisplatin) for Treatment of Lung Cancer," Lipids, Liposomes & Biomembranes 2005: New Technologies, University of British Columbia, Vancouver, Canada, p. 78 (Jul. 26-30, 2005).

Platinoi® -AQ (cisplatin injection), Drug Information Label (1999).

Possmayer, F. et al., "The pulmonary surfactant: Control of fluidity at the air-liquid interface," In: Membrane Fluidity, Kates M. et al. (eds.), pp. 57-67, Clifton, NJ, Humana Press (1980).

Potkul, R. K. et al., "Toxicities in rats with free versus liposomal encapsulated cisplatin," Am. J. Obstet. Gynecol., 164(2):652-658 (1991).

Prestayko, A. W. et al., "Cisplatin (cis-diamminedichloroplatinum II)," Cancer Treatment Reviews, 6(1):17-39 (1979).

Rahman, A. et al., "Liposomal protection of adriamycin-induced cardiotoxicity in mice[1]," Cancer Research, 40:1532-1537 (1980).

Richardson, V. J. et al., "Tissue distribution and tumour localization of 99m-technetium-labelled liposomes in cancer patients," Br. J. Cancer, 40:35-43 (1979).

Ritter, J. et al., "Osteosarcoma," Annals of Oncology, 21(7):vii320-vii325 (2010).

Rowinsky, E. K. et al., "Paclitaxel (Taxol)," N. Engl. J. Med., Review Article, 332(15):1004-1014 (1995).

Ryman, B. E. et al., "Liposomes—Further Considerations of their Possible Role as Carriers of Therapeutic Agents," Targeting of Drugs, Gregoriadis, G. et al. (eds.), Plenum Press, New York, pp. 235-248 (1982).

Schiller, J. H. et al., "Current standards of care in small-cell and non-small-cell lung cancer," Oncology, 61(1):3-13 (2001).

Schwartsmann, G. et al., "A phase I trial of cisplatin plus decitabine, a new DNA-hypomethylating agent, in patients with advanced solid tumors and a follow-up early phase II evaluation in patients with inoperable non-small cell lung cancer," Investigational New Drugs, 18(1):83-91 (2000).

Shek, P. N. et al., "Liposomes: a new generation of drug and vaccine carriers," Mod. Med. Canada, 41(4):314-326 (1986).

Smondyrev, A. M. et al., "Structure of dipalmitoylphosphatidylcholine/cholesterol bilayer at low and high cholesterol concentrations: Molecular dynamics simulation," Biophysical Journal, 77:2075-2089 (1999).

Stathopoulos, G. P. et al., "Paclitaxel combined with cis-platin as second-line treatment in patients with advanced non-small cell lung cancers refractory to cis-platin," Oncology Reports, 6:797-800 (1999).

Stathopoulos, G. P. et al., "Pharmacokinetics and adverse reactions of a new liposomal cisplatin (Lipoplatin): Phase I study," Oncology Reports, 13:589-595 (2005).

Steerenberg, P. A. et al., "Liposomes as drug carrier system for cis-diamminedichloroplatinum (II). II. Antitumor activity in vivo, induction of drug resistance, nephrotoxicity and Pt distribution," Cancer Chemother. Pharmacol., 21(4):299-307 (1988).

Steerenberg, P. A. et al., "Liposomes as a drug carrier system for cis-diamminedichloroplatinum (II). I. Binding capacity, stability and tumor cell growth inhibition in vitro," International Journal of Pharmaceutics, 40:51-62 (1987).

Sur, B. et al., "Effect of liposomal encapsulation of cis-platinum diamminodichloride in the treatment of ehrlich ascites carcinoma," Oncology, 40(5):372-376 (1983).

Szoka, Jr. et al., "Comparative properties and methods of preparation of lipid vesicles (Liposomes)," Ann. Rev. Biophys. Bioeng., 9:467-508 (1980).

Tom, J. W. et al., "Particle formation with supercritical fluids—A review," Journal of Aerosol Science, 22(5):555-584 (1991).

Vadiei, K. et al., "Pharmacokinetics of liposome-entrapped cis-bis-neodecanoato-trans-R,R-1,2-diaminocyclohexane platinum(II) and cisplatin given i.v. and i.p. In the rat," Cancer Chemotherapy and Pharmacology, 30(5):365-369 (1992).

Yokes, E. E. et al., "A phase I study of Stealth cisplatin (SPI-77) and vinorelbine in patients with advanced non-small-cell lung cancer," Clinical Lung Cancer, 2(2):128-132 (2000).

Wang, S. et al., "Feasibility and long-term efficacy of video-assisted thoracic surgery for unexpected pathologic N2 disease in non-small cell lung cancer," Ann. Thorac. Med., 8(3):170-175 (2013).

Ward, W. G. et al., "Pulmonary metastases of stage IIB extremity osteosarcoma and subsequent pulmonary metastases," J. Clin. Oncol., 12(9):1849-1858 (1994).

Weiss, R. B. et al., "New cisplatin analogues in development. A review," Drugs, 46(3):360-377 (1993).

Wittgen, B. P. H. et al., "Assessing a system to capture stray aerosol during inhalation of nebulized liposomal cisplatin," Journal of Aerosol Medicine, 19(3):385-391 (2006).

Wittgen, B. P. H. et al., "Phase I study of aerosolized SLIT cisplatin in the treatment of patients with carcinoma of the lung," Clin. Cancer Res., 13(8):2414-2421 (2007).

Zhang, X. et al., "Periosteal stem cells are essential for bone revitalization and repair," J. Musculoskelet. Neuronal. Interact., 5(4):360-362 (2005).

Zhang, Y. et al., "The development of targeted therapy in small cell lung cancer," J. Thoracic Dis., 5(4):538-548 (2013).

Zou, Y. et al., "LB-268. Pharmacokinetics and organ distribution of liposomal cisplatin administered intravenously and intraperitoneally," Proceedings American Association Cancer Research (2005).

* cited by examiner

METHODS OF TREATING CANCER WITH HIGH POTENCY LIPID-BASED PLATINUM COMPOUND FORMULATIONS ADMINISTERED INTRAPERITONEALLY

RELATED APPLICATIONS

This application is a continuation-in-part of U.S. patent application Ser. No. 11/592,754, filed on Nov. 3, 2006, now abandoned, which claims the benefit of priority to U.S. Provisional Patent Application Ser. No. 60/734,474, filed Nov. 8, 2005, and which are both hereby incorporated by reference in their entirety.

INTRODUCTION

Parenteral routes of administration involve injections into various compartments of the body. Parenteral routes include intravenous (iv), i.e. administration directly into the vascular system through a vein; intra-arterial (ia), i.e. administration directly into the vascular system through an artery; intraperitoneal (ip), i.e. administration into the abdominal cavity; subcutaneous (sc), i.e. administration under the skin; intramuscular (im), i.e. administration into a muscle; and intradermal (id), i.e. administration between layers of skin. The parenteral route is preferred over oral ones in many occurrences. For example, when the drug to be administered would partially or totally degrade in the gastrointestinal tract, parenteral administration is preferred. Similarly, where there is need for rapid response in emergency cases, parenteral administration is usually preferred over oral.

Regional delivery of chemotherapy into the peritoneal space via ip administration has been found to be a safe and effective treatment for locally recurrent cancers such as, for example, ovarian and colon cancers.

The concept of the intraperitoneal administration of antineoplastic agents in the management of cancers such as ovarian cancer has attracted the interest of numerous investigators. In fact, alkylating agents, the first cytotoxic drugs to be introduced into clinical practice, were initially examined for intraperitoneal delivery in the early 1950s. Markman M., *Cancer Treat Rev.*, 1986, 13, 219-242.

However, it was not until the late 1970s that both the problems and potential of regional drug administration in the treatment of ovarian cancer began to be thoroughly explored. Markman M., *Cancer Treat Rev.*, 1986, 13,219-242; Markman M., *Semin. Oncol.*, 1991, 18(suppl 3), 248-254. An important event in the development of a rational strategy for the examination of intraperitoneal drug delivery was the publication of a now-classic paper by Dedrick et al., from the National Cancer Institute where, for the first time, a sound pharmacokinetic rationale for this approach in the management of ovarian cancer was presented. Dedrick R L, Myers C E, Bungay P M et al., *Cancer Treat. Rep.*, 1978, 62, 1-9.

Cisplatin—cis-diamine-dichloroplatinum (II)—is one of the more effective anti-tumor agents used in the systemic treatment of cancers. This chemotherapeutic drug is highly effective in the treatment of tumor models in laboratory animals and in human tumors, such as endometrial, bladder, ovarian and testicular neoplasms, as well as squamous cell carcinoma of the head and neck (Sur, et al., 1983 Oncology 40(5): 372-376; Steerenberg, et al., 1988 Cancer Chemother Pharmacol. 21(4): 299-307). Cisplatin is also used extensively in the treatment of lung carcinoma, both SCLC and NSCLC (Schiller et al., 2001 Oncology 61(Suppl 1): 3-13). Other active platinum compounds (defined below) are useful in cancer treatment.

Like other cancer chemotherapeutic agents, active platinum compounds such as cisplatin are typically highly toxic. The main disadvantages of cisplatin are its extreme nephrotoxicity, which is the main dose-limiting factor, its rapid excretion via the kidneys, with a circulation half life of only a few minutes, and its strong affinity to plasma proteins (Freise, et al., 1982 Arch Int Pharmacodyn Ther. 258(2): 180-192).

Attempts to minimize the toxicity of active platinum compounds have included combination chemotherapy, synthesis of analogues (Prestayko et al., 1979 Cancer Treat Rev. 6(1): 17-39; Weiss, et al., 1993 Drugs. 46(3): 360-377), immunotherapy and entrapment in liposomes (Sur, et al., 1983; Weiss, et al., 1993). Antineoplastic agents, including cisplatin, entrapped in liposomes have a reduced toxicity, relative to the agent in free form, while retaining antitumor activity (Steerenberg, et al., 1987; Weiss, et al., 1993).

Cisplatin, however, is difficult to efficiently entrap in liposomes or lipid complexes because of the bioactive agent's low aqueous solubility, approximately 1.0 mg/ml at room temperature, and low lipophilicity, both of which properties contribute to a low bioactive agent/lipid ratio.

Liposomes and lipid complexes containing cisplatin suffer from another problem—stability of the composition. In particular, maintenance of bioactive agent potency and retention of the bioactive agent in the liposome during storage are recognized problems (Freise, et al., 1982; Gondal, et al., 1993; Potkul, et al., 1991 Am J Obstet. Gynecol. 164(2): 652-658; Steerenberg, et al., 1988; Weiss, et al., 1993) and a limited shelf life of liposomes containing cisplatin, on the order of several weeks at 4° C., has been reported (Gondal, et al., 1993 Eur J Cancer. 29A(11): 1536-1542; Potkul, et al., 1991).

Alberts et al. have shown that as compared with iv cisplatin, ip cisplatin significantly improves survival and has significantly fewer toxic effects in patients with stage III ovarian cancer and residual tumor masses of 2 cm or less. Alberts D. S. et al., *New England Journal of Medicine*, 1996, 335(26), 1950-5. However, ip cisplatin has several disadvantages such as no improvement in nephrotoxicity which is the dose-limiting toxicity.

Additionally, both preclinical and clinical data have firmly established that any benefits associated with employing the intraperitoneal route of drug delivery in the treatment of ovarian cancer are limited to a relatively well-defined small subset of patients with this malignancy. Markman M., *Cancer Treat Rev.*, 1986, 13,219-242; Markman M., *Semin. Oncol.*, 1991, 18(*suppl* 3), 248-254; Markman M, Reichman B, Hakes T et al., *J. Clin. Oncol.*, 1991, 9, 1801-1805. For example, in a series of patients treated at the Memorial Sloan-Kettering Cancer Center (MSKCC) with combination cisplatin-based therapy as salvage treatment of advanced ovarian cancer, 32% (17/50) of individuals whose largest residual tumor mass measured ≤1 cm in maximum diameter at the initiation of ip therapy achieved a surgically documented complete response, compared to only 5% (2/39) of patients with at least one tumor mass >1 cm in maximum diameter. Markman M, Reichman B, Hakes T et al., *J. Clin. Oncol.*, 1991, 9, 1801-1805. Clearly more is needed than just direct routes of administration to overcome the increasingly deleterious effects of cancer.

In addition to cisplatin, a number of other antineoplastic agents have been examined for safety and potential efficacy when delivered by the ip route as salvage treatment of ovarian cancer. These include carboplatin, paclitaxel, mitoxantrone, doxorubicin, mitomycin-C, 5-fluorouracil, methotrexate, thiotepa, recombinant interferon-α, recombinant interferon-γ, interleukin 2 and tumor necrosis factor. Markman M., *Can-* cer *Treat Rev.,* 1986, 13, 219-242; Markman M., *Semin. Oncol.,* 1991, 18(suppl 3), 248-254; Markman M, Reichman B, Hakes T et al., *J. Clin. Oncol.,* 1991, 9, 1801-1805; Markman M., *Regional antineoplastic drug delivery in the management of malignant disease. Baltimore: The Johns Hopkins University Press,* 1991; Berek J. S., Markman M., *Int. J. Gynecol. Cancer,* 1992, 1, 26-29; Markman M, Berek J. S., *Int. J. Gynecol. Cancer,* 1992, 1, 30-34; Alberts D. S., Liu P. Y., Hannigan E. V. et al., *Proc. Am. Soc. Clin. Oncol.,* 1995, 14, 273a; Rowinsky E. K., Donehower R. C., N. *Engl. J. Med.,* 1995, 332, 1004-1014. Combination regimens have also been explored.

Despite the advances made with ip administration of platinum compounds, the dose limiting toxicity and low drug level in targeted tissues of platinum compounds make most therapies fail to improve patients' life-expectancy. It would be advantageous to develop a platinum compound composition with potency higher than its aqueous solubility limit at room temperature. High potency lipid complexed platinum compound compositions would reduce the liquid dose volume for a given dose, consequently reducing the dosing time (duration).

SUMMARY OF THE INVENTION

It is an object of the present invention to provide a method of treating cancer comprising administering platinum compounds as part of a high potency lipid-based composition with lower sub-acute toxicity, in some cases by as much as two times, than when the platinum compound is administered without the lipid-based composition.

It is also an object of the present invention to provide a high potency lipid-based platinum compound composition wherein the potency is higher than the aqueous solubility of the platinum compound at room temperature.

It is also an object of the present invention to treat cancer using a high potency lipid-based platinum compound composition to reduce the volume of composition that has to be administered to achieve the same level of effectiveness.

It is also an object of the present invention to treat cancer by introducing platinum compounds as high potency lipid based compositions regionally to bypass gastrointestinal degradation that is often associated with oral administration.

The subject invention results from the realization that high potency lipid-based platinum compound compositions presented herein can be effectively administered intraperitoneally.

In one embodiment, the present invention relates to a method of treating cancer in a patient comprising administering intraperitoneally to a patient in need thereof a cancer treating effective amount of a composition comprising a lipid-complexed active platinum compound, wherein the lipid complexed active platinum compound has a lipid to drug ratio of less than about 1 by weight, e.g. about 0.10 to 1, wherein the lipid-complexed active platinum compound comprises at least one lipid and at least one active platinum compound.

In some embodiments, wherein lipid-complexed active platinum compound has an average volume-weighted diameter of about 0.5 to about 20 microns.

In some embodiments, the composition further comprises a liposome. The liposome may comprise at least one lipid, and may further comprise at least one active platinum compound.

In some embodiments, the composition administered in the aforementioned method has a concentration of the platinum compound greater than about 1.2 mg/ml. In a further embodiment the platinum compound concentration is about 3 mg/ml.

In a further embodiment the platinum compound concentration is about 5 mg/ml.

In a further embodiment the present invention relates to the aforementioned method, wherein the cancer is selected from the following: melanoma, testis (germ cell), osteosarcoma, soft tissue sarcoma, thyroid cancer, colon cancer, ovarian cancer, cancer of the kidney, breast cancer, colorectal cancer, prostate cancer, bladder cancer, uterine cancer, lung cancer, stomach cancer, liver cancer, spleen cancer, endometrial, or squamous cell carcinomas of the head and neck. In a further embodiment the cancer is ovarian or colon cancer.

In a further embodiment the present invention relates to the aforementioned method, wherein the patient is a human. In a further embodiment, the composition comprising a lipid-complexed platinum compound is administered to the patient at least once every three weeks. In a further embodiment, the composition is administered to the patient at least twice every three weeks. In a further embodiment, the composition is administered to the patient at least three times every three weeks.

In a further embodiment, the amount of platinum compound in the composition is 60 mg/m$^2$ or greater, 100 mg/m$^2$ or greater, 140 mg/m$^2$ or greater, or 180 mg/m$^2$ or greater. In a further embodiment, the amount is 100 mg/m$^2$ or greater, and the composition is administered to the patient at least once every three weeks.

These embodiments of the present invention, other embodiments, and their features and characteristics, will be apparent from the description, drawings and claims that follow.

DETAILED DESCRIPTION OF THE INVENTION

Definitions

Figure 1:
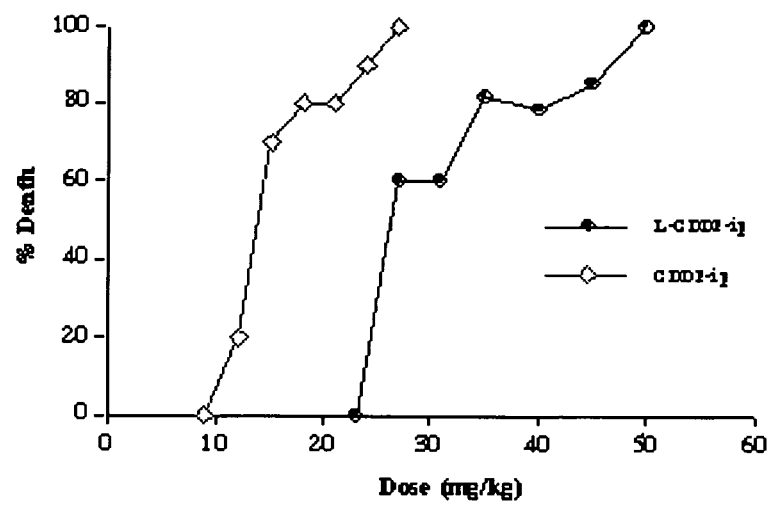
FIG. 1 depicts the large decrease in toxicity of ip administration of lipid-complexed cisplatin (L-CDDP-ip) as compared to ip administration of cisplatin (CDDP-ip).

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "bioavailable" is art-recognized and refers to a form of the subject invention that allows for it, or a portion of the amount administered, to be absorbed by, incorporated to, or otherwise physiologically available to a subject or patient to whom it is administered.

The term "cancer treating effective amount" as used herein refers to the amount of lipid-complexed platinum compound composition effective for the treatment of cancer. In one embodiment the cancer treating effective amount of lipid-complexed platinum compound composition is typically about 100 mg/m$^2$ for ip delivery in a human.

The term "CDDP" stands for cis diamminedichloroplatinum which is used interchangeably with "cisplatin."

The term "hydrophobic matrix carrying system" is a lipid/solvent mixture prepared during the solvent infusion process described below.

The term "intraperitoneal" or "intraperitoneally" or "ip" as used herein refers to administration of a therapeutic agent, such as, for example, an antineoplastic compound, such as a platinum compound, to the peritoneal cavity of a patient. The term "peritoneal cavity" as used herein refers to the serous membrane lining the abdominopelvic walls and investing the viscera.

The term "L-CDDP" stands for a lipid complexed composition of cis diamminedichloroplatinum and is used interchangeably with "lipid-complexed cisplatin."

The terms "lipid-complexed platinum compound" as used herein refers to a composition comprising a lipid and a platinum compound. In some embodiments, the lipid complexed active platinum compound comprises a lipid bilayer, where the lipid bilayer encapsulates or entraps the platinum compound. Exemplary lipid-complexed platinum compounds are described in U.S. patent application Ser. No. 12/027,752, filed Feb. 7, 2008, which is hereby incorporated by reference in its entirety.

The term "mammal" is known in the art, and exemplary mammals include humans, primates, bovines, porcines, canines, felines, and rodents (e.g., mice and rats).

A "patient," "subject" or "host" to be treated by the subject method may mean either a human or non-human animal.

The term "pharmaceutically-acceptable salts" is art-recognized and refers to the relatively non-toxic, inorganic and organic acid addition salts of compounds, including, for example, those contained in compositions of the present invention.

The term "solvent infusion" is a process that includes dissolving one or more lipids in a small, preferably minimal, amount of a process compatible solvent to form a lipid suspension or solution (preferably a solution) and then adding the solution to an aqueous medium containing bioactive agents. Typically a process compatible solvent is one that can be washed away in a aqueous process such as dialysis. The composition that is cool/warm cycled is preferably formed by solvent infusion. Alcohols are preferred as solvents, with ethanol being a preferred alcohol.

"Ethanol infusion," is a type of solvent infusion that includes dissolving one or more lipids in a small, preferably minimal, amount of ethanol to form a lipid solution and then adding the solution to an aqueous medium containing bioactive agents. A "small" amount of solvent is an amount compatible with forming liposomes or lipid complexes in the infusion process.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic index" is an art-recognized term which refers to the ratio of a quantitative assessment of toxicity to a quantitative assessment of efficacy of a drug, e.g. $LD_{50}/ED_{50}$ in the case of animals. The term "$LD_{50}$" is art recognized and refers to the amount of a given toxic substance that will elicit a lethal response in 50% of the test organisms. This is sometimes also referred to as the median lethal dose. The term "$ED_{50}$" is art recognized and refers to the median effective dose.

The term "treating" is art-recognized and refers to curing as well as ameliorating at least one symptom of any condition or disease.

Introduction

Typical human parenteral dosage amounts with current commercial cisplatin solutions (e.g. Platinol from Bristol Myers Squibb) are about 100 mg/m$^2$ (unit dose) administered once every 3 weeks intravenously for a single drug therapy. Dose limiting factors include of course unwanted side effects (e.g. renal toxicity, severe vomiting, etc.). With higher potency platinum compound compositions, it would take less time to administer the platinum compound solution because less volume would have to be administered to achieve an equal amount of platinum compound. For example, a 100 mg/m$^2$ dosage with a human body surface of 1.6 to 2 m$^2$ (for the sake of this example, lets use 2 m$^2$) would require administering 200 mg of platinum compound at one time. Using current commercial cisplatin solutions (1 mg/ml, the solubility limit at room temperature) requires infusing 200 ml of cisplatin solution into the body. At 5× the potency (5 mg/ml) only ⅕ the volume or 40 ml would need to be infused, which also means the process would take ⅕ the amount of time.

Presented herein are compositions of a platinum compound that exceed their ordinary solubility limitations of 1 mg/ml and methods of treating cancer therewith. The greater potency of the platinum compound compositions is achieved by preparing the platinum compound in compositions comprising a lipid-complexed compound. The high potency lipid-complexed platinum compound compositions of the present invention and methods of treating cancer therewith also benefit from the fact that the lipid-complexed compositions decrease the sub-acute toxicity of the platinum compound allowing even higher doses of platinum to be administered.

Compositions

The lipids used in forming lipid complexes and liposomes for ip delivery of an antineoplastic agent may be synthetic, semi-synthetic or naturally-occurring lipids, including phospholipids, tocopherols, sterols, fatty acids, glycoproteins such as albumin, negatively-charged lipids and cationic lipids.

Liposomes are completely closed lipid bilayer membranes containing an entrapped aqueous volume. Liposomes used for the parenteral delivery of an antineoplastic compound may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

Liposomes and lipid complexes can be produced by a variety of methods (for a review, see, e.g., Cullis et al. (1987)). Bangham's procedure (J. Mol. Biol. (1965)) produces ordinary multilamellar vesicles (MLVs). Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation.

Unilamellar vesicles can be produced from MLVs by a number of techniques, for example, the extrusion of Cullis et al. (U.S. Pat. No. 5,008,050) and Loughrey et al. (U.S. Pat. No. 5,059,421)). Sonication and homogenization cab be so used to produce smaller unilamellar liposomes from larger liposomes (see, for example, Paphadjopoulos et al. (1968); Deamer and Uster (1983); and Chapman et al. (1968)).

The original liposome preparation of Bangham et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys, Acta., 1967, 135:624-638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes may be found in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

Other techniques that are used to prepare vesicles include those that form reverse-phase evaporation vesicles (REV), Papahadjopoulos et al., U.S. Pat. No. 4,235,871. Another class of liposomes that may be used are those characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilamellar vesicles (FATMLV) as described above.

A variety of sterols and their water soluble derivatives such as cholesterol hemisuccinate have been used to form liposomes; see specifically Janoff et al., U.S. Pat. No. 4,721,612, issued Jan. 26, 1988, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. 87/02219, published Apr. 23, 1987, entitled "Alpha Tocopherol-Based Vesicles".

Liposomes can also be prepared by the methods disclosed in copending U.S. patent application Ser. No. 10/383,004, filed Mar. 5, 2003; Ser. No. 10/634,144, filed Aug. 4, 2003; Ser. No. 10/224,293, filed Aug. 20, 2002; and Ser. No. 10/696,389, filed Oct. 29, 2003, the specifications of which are incorporated herein in their entirety.

Another method of preparing liposomes or lipid complexes is the "solvent infusion" process. Solvent infusion is a process that includes dissolving one or more lipids in a small, preferably minimal, amount of a process compatible solvent to form a lipid suspension or solution (preferably a solution) and then adding the solution to an aqueous medium containing, for example, platinum compounds. Typically a process compatible solvent is one that can be washed away in an aqueous process such as dialysis. The composition that is cool/warm cycled is preferably formed by solvent infusion, with ethanol infusion being preferred.

The process for producing lipid-complexed platinum compound compositions may comprise mixing a platinum compound with an appropriate hydrophobic matrix and subjecting the mixture to one or more cycles of two separate temperatures. The process is believed to form active platinum compound associations.

In aqueous solution, cisplatin forms large insoluble aggregates with a diameter of greater than a few microns. In the presence of a amphipathic matrix system, such as a lipid bilayer, cisplatin-lipid associations form. For example, the associations may be formed in the internal aqueous space, the hydrocarbon core region of a lipid bilayer, or the liposome interface or headgroup. During the warming cycle of the process, it is believed that cisplatin is returned to solution at a greater rate in aqueous regions of the process mixture than from the lipid-complex. As a result of applying more than one cool/warm cycle, cisplatin accumulates further into the lipid-complex. Without limiting the invention to the proposed theory, experimentation indicates that the cisplatin-lipid associations cause the immediate surroundings of the interfacial bilayer region to be more hydrophobic and compact. This results in a high level of entrapment of active platinum compound as cooling and warming cycles are repeated.

The process comprises combining the platinum compound with a hydrophobic matrix carrying system and cycling the solution between a warmer and a cooler temperature. Preferably the cycling is performed more than one time. More preferably the step is performed two or more times, or three or more times. The cooler temperature portion of cycle can, for example, use a temperature from about −25° C. to about 25° C. More preferably the step uses a temperature from about −5° C. to about 25° C. or from about 1° C. to about 20° C. For manufacturing convenience, and to be sure the desired temperature is established, the cooler and warmer steps can be maintained for a period of time, such as approximately from 5 to 300 minutes or 30 to 60 minutes. The step of warming comprises warming the reaction vessel to from about 4° C. to about 70° C. More preferably the step of warming comprises heating the reaction vessel to about 45° C. or to about 55° C. The above temperature ranges are particularly preferred for use with lipid compositions comprising predominantly diphosphatidycholine (DPPC) and cholesterol.

Another way to consider the temperature cycling is in terms of the temperature differential between the warmer and the cooler steps of the cycle. This temperature differential can be, for example, about 25° C. or more, such as a differential from about 25° C. to about 70° C., preferably a differential from about 40° C. to about 55° C. The temperatures of the cooler and higher temperature steps are selected on the basis of increasing entrapment of active platinum compound. Without being limited to theory, it is believed that it is useful to select an upper temperature effective substantially increase the solubility of active platinum compound in the processed mixture. Preferably, the warm step temperature is about 50° C. or higher. The temperatures can also be selected to be below and above the transition temperature for a lipid in the lipid composition.

The temperatures appropriate for the method may, in some cases, vary with the lipid composition used in the method, as can be determined by ordinary experimentation. The temperatures of the warming and cooling steps are selected on the basis of increasing entrapment of active platinum compound. Without being limited by any particular theory, it is believed that it is useful to select an upper temperature effective substantially increase the solubility of active platinum compound in the process mixture. During repetitive cooling/heating, bioactive agents are solubilized and crystallized repetitively. As soluble drug is cooled, some portion enters complexes with the lipid while the remainder precipitates. On subsequent heating, unencapsulated bioactive agent that is crystallized becomes soluble again. Importantly, active platinum compound that has been encapsulated in the lipid complex substantially stays in the lipid complex during the heating and cooling cycling (e.g. it leaks at such a slow rate that no appreciable amount leaves the lipid complex during the heating phase of this process).

For example, as the temperature is increased during the warming step of the cycle, the active platinum compound, such as cisplatin, dissolves. During the cooling step, the cisplatin in the aqueous phase precipitates out of solution to a greater extent that the cisplatin associated with the lipid bilayers, thereby increasing the amount of lipid-associated cisplatin with each heating and cooling cycle. Additionally, solubility of cisplatin is highly temperature-dependent. Lowering 15° in temperature of a cisplatin solution decreases the soluble concentration by about 50%. In other words, solubility limiting concentration increases with increasing temperature by about 3% per degree increase in temperature of aqueous cisplatin. In addition, the aggregate (crystal)-to-monomer transition temperature (solubilizing temperature) is higher than the monomer-to-aggregate (crystal) transition temperature (crystallizing temperature) by about 15 to 20° C.

Transplatin solubility is poorer than cisplatin, but it is also temperature-dependent. Lowering the temperature by about 15° C. decreases the soluble concentration of transplatin by about 50%. The aggregate (crystal)-to-monomer transition temperature (solubilizing temperature) is higher than the monomer-to-aggregate (crystal) transition temperature (crystallizing temperature) by about 20 to 30° C.

Experimental results strongly indicate that the physical state of cisplatin is solid (aggregates) or lipid bound since the concentration of cisplatin is much higher than the solubility limit. Results further indicate that process does not require freezing the compositions, but that cooling to temperature higher than the freezing point of water is effective. Results further indicated that an entrapment efficiency achieved by 3-cycles was similar to that achieved by 6-cycles of cooling and warming cycles, which indicated that 3 cycles of temperature treatment was sufficient to achieve high levels of active platinum compound entrapment.

Results further indicate that the process can be scaled-up while increasing process efficiency in entrapping cisplatin. Thus, the invention further provides processes that are conducted to provide an amount adapted for total administration (in appropriate smaller volume increments) of 200 or more mLs, 400 or more mLs, or 800 or more mLs. All else being the same, it is believed that the larger production volumes generally achieve increased efficiency over smaller scale processes. While such volume is that appropriate for administration, it will be recognized that the volume can be reduced for storage.

Results further indicate that the lipid-complexed cisplatin made by the method of the invention can retain entrapped cisplatin with minimal leakage for over one year. This is a further demonstration of the uniqueness in the composition, indicating that the cisplatin is bound within the liposome structure and not free to readily leak out.

The process of the present invention may further comprise separating the components of the product of the aforementioned process. For example, in some embodiments, the process provides both the aforementioned lipid-complexed active platinum compound and the aforementioned liposome. In certain embodiments, the portion of the product comprising the lipid-complexed active platinum compound, referred to herein as "the heavy fraction" may be separated from the portion comprising the liposome, referred to herein as "the light fraction." Methods of separating include allowing the heavy product to settle over a period of time, or centrifuging the product.

The lipid to platinum compound ratio (L/D) seen in the lipid-complexed platinum compounds used in the present invention may be less than about 1 by weight. For example the L/D ratio can be about 0.10 to 1 by weight, wherein the lipid-complexed active platinum compound comprises at least one lipid and at least one active platinum compound. In some embodiments, the lipid to drug ratio is about 0.10 to about 0.50 by weight. In some embodiments, the lipid to drug ratio is about 0.15 to about 0.45 by weight, and in other embodiments, the lipid to drug ratio is about 0.20 to 0.40 by weight. In some embodiments, the lipid to drug ratio is about 0.2 by weight.

The lipid-complexed active platinum compound may have an average volume-weighted diameter of about 0.5 to about 20 microns. In some embodiments, the average volume-weighted diameter is about 1 to about 15 microns, or about 2 to about 10 microns. In other embodiments, the average volume-weighted diameter is about 3, 4, 5, or 6 microns.

In some embodiments, the concentration of the active platinum compound in the composition is greater than about 1.2 mg/mL, for example about 1.2 to about 20 mg/mL. In other embodiments, the concentration of the active platinum compound is about 1.2 to 10 mg/mL, about 1.5 to about 5 mg/mL, about 2.0 to about 4 mg/mL, or about 3.0 to 2.5 mg/mL. In other embodiments, the concentration is about 2, about 3, or about 5 mg/mL.

In some embodiments, the composition comprising the lipid-complexed active platinum compound further comprises a liposome. As explained in greater detail in the examples below, the liposome comprises at least one lipid. The lipid may be the same as or different from the lipid in the lipid-complexed active platinum compound. In some embodiments, the liposome further comprises an active platinum compound, wherein the active platinum compound can be the same as or different from the active platinum compound of the lipid-complexed active platinum compound. The active platinum compound may be entrapped in the liposome.

In some embodiments, the liposomes have an average diameter of about 0.1 to about 1 micron, 0.1 to about 0.5 microns, about 0.2 to about 0.5 microns, or about 0.2 to about 0.3 microns.

When the lipid composition further comprises a liposome, the lipid-complexed active platinum compound may contain about 70 to about 100% of the total active platinum compound in the composition. In other embodiments, the lipid-complexed active platinum compound contains about 75 to about 99%, about 75 to about 95%, or about 80 to about 90% of the total active platinum compound in the composition. In some embodiments, the liposome contains about 0 to about 30% of the total active platinum compound in the composition. In other embodiments, the liposome may contain about 0.5 to about 25%, about 1 to about 20%, or about 5 to 10% of the total active platinum compound.

When the composition further comprises a liposome, the lipid-complexed active platinum compound may contain about 0.1 to about 5% of the total lipid in the composition. In some embodiments, the lipid-complexed active platinum compound contains about 0.25 to about 3%, or about 0.5 to about 2% of the total lipid. In some embodiments, the liposome contains about 75 to about 99.5%, about 80 to about 95%, or about 85 to about 95% of the total lipid in the composition.

When present in the composition, the liposome may have a lipid to active platinum compound ratio of about 100:1 to about 400:1 by weight. In other embodiments, the lipid to active platinum compound ratio of the liposome is about 200:1 to about 400:1, about 200: to 300:1 about 250:1 to 300:1 or about 250:1 by weight.

In some embodiments, the composition comprising a lipid-complexed active platinum compound and a liposome has an active platinum compound concentration of greater than about 1.2 mg/mL, for example, the concentration may be about 1.2 to about 20 mg/mL, about 1.2 to about 10 mg/mL, about 1.5 to about 5 mg/mL, about 2.0 to about 4 mg/mL, or about 3.0 to about 2.5 mg/mL. In other embodiments, the concentration is about 2, about 3, or about 5 mg/mL.

An "active platinum" compound is a compound containing coordinated platinum and having antineoplastic activity. Additional active platinum compounds include, for example, carboplatin and DACH-platinum compounds such as oxaliplatin. In certain embodiments, the active platinum compounds in the composition is selected from the group consisting of cisplatin, carboplatin, oxaliplatin, iproplatin, tetraplatin, transplatin, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum (IV)) and JM335 (trans-amminedichloro(cyclohexylamine) dihydroxoplatinum(IV)). In some embodiments, the active platinum compound is cisplatin.

The platinum compounds that may be used in the composition for the aforementioned method include any compound that exhibits the property of preventing the development, maturation, or spread of neoplastic cells. Non-limiting examples of platinum compounds include cisplatin, carboplatin (diammine(1,1-cyclobutanedicarboxylato)-platinum (II)), tetraplatin (ormaplatin) (tetrachloro(1,2-cyclohexanediamine-N,N')-platinum(IV)), thioplatin (bis(O-ethyldithiocarbonato)platinum(II)), satraplatin, nedaplatin, oxaliplatin, heptaplatin, iproplatin, transplatin, lobaplatin, cis-aminedichloro(2-methylpyridine) platinum, JM118 (cis-amminedichloro (cyclohexylamine)platinum(II)), JM149 (cis-amminedichloro(cyclohexylamine)-trans-dihydroxoplatinum(IV)), JM216 (bis-acetato-cis-amminedichloro(cyclohexylamine) platinum(IV)), JM335 (trans-amminedichloro(cyclohexylamine)dihydroxoplatinum(IV)), and (trans, trans, trans)bis-mu-(hexane-1,6-diamine)-mu-[diamine-platinum(II)]bis[diamine(chloro) platinum(II)]tetrachloride. In another embodiment the platinum compound is cisplatin. Depending on the environment, cisplatin may exist in a cationic aquated form wherein the two negatively charged chloride atoms have been displaced by two neutral water molecules. Because the aquated form of cisplatin is cationic, anionic lipids such as glycerols help to stabilize the lipid-complexed composition, but may also hinder release on the cisplatin. The non-aquated, neutral form of cisplatin is more difficult to stabilize but has different release kinetics. It is considered an advantage of the present invention that in certain embodiments the lipid-complexed cisplatin compositions comprise neutral cisplatin and neutral lipids. Because of the equilibrium between neutral, non-aquated cisplatin and cationic, aquated cisplatin, one may favor neutral, non-aquated cisplatin by preparing a composition with a low pH and high NaCl concentration. In this embodiment a substantial amount of the cationic, aquated form of cisplatin would not form until the neutral, non-aquated cisplatin was delivered into the interior of a cell.

In certain embodiments, the active platinum compound is selected from the group consisting of cisplatin, carboplatin, oxaliplatin, iproplatin, tetraplatin, transplatin, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)) and JM335 (trans-amminedichloro(cyclohexylamine)dihydroxoplatinum(IV)). In some embodiments, the active platinum compound is cisplatin, transplatin, carboplatin, or oxaliplatin, while in other embodiments, the active platinum compound is cisplatin.

In other embodiments, other therapeutic agents may be used with the platinum compounds. The other therapeutic agents may have antineoplastic properties. Non-limiting examples of antineoplastic compounds include altretamine, amethopterin, amirubicin, annamycin, arsenic trioxide, asparaginase, BCG, benzylguanine, bisantrene, bleomycin sulfate, busulfan carmustine, cachectin, chlorabucil, 2-chlorodeoxyadenosine, cyclophosphamide, cytosine arabinoside, dacarbazine imidazole carboxamide, dactinomycin, daunomycin, 3'-deamino-3'-morpholino-13-deoxo-10-hydroxycaminomycin, 4-demethoxy-3-deamino-3-aziridinyl-4-methylsulphonyl-daunorubicin, dexifosfamide, dexamethasone, diarizidinylspermine, dibromodulcitol, dibrospidium chloride, 1-(11-dodecylamino-10-hydroxyundecyl)-3,7-dimethylxanthine, doxorubicin, elinafide, epipodophyllotoxin, estramustine, floxuridine, fluorouracil, fluoxymestero, flutamide, fludarabine, fotemustine, galarubicin, glufosfamide, goserelin, GPX100, hydroxyurea, idarubicin HCL, ifosfamide, improsulfan tosilate, isophosphamide, interferon alfa, interferon alfa 2a, interferon alfa 2b, interferon alfa n3, interferon gamma, interleukin 2, irinotecan, irofulven, leucovorin calcium, leuprolide, levamisole, lomustine, megestrol, L-phenylalanie mustard, L-sarcolysin, melphalan hydrochloride, mechlorethamine, MEN10755, mercaptopurine, MESNA, methylprednisolone, methotrexate, mitomycin, mitomycin-C, mitoxantrone, nimustine, paclitaxel, pinafide, pirarubicin, plicamycin, prednimustine, prednisone, procarbazine, profiromycin, pumitepa, ranimuistine, sertenef, streptozocin, streptozotocin, tamoxifen, tasonermin, temozolomide, 6-thioguanine, thiotepa, tirapazimine, triethylene thiophosphoramide, trofosfamide, tumor necrosis factor, valrubicin, vinblastine, vincristine, vinorelbine tartrate, and zorubicin.

Also included as suitable platinum compounds used in the methods of the present invention are pharmaceutically acceptable addition salts and complexes of platinum compounds. In cases wherein the compounds may have one or more chiral centers, unless specified, the present invention comprises each unique racemic compound, as well as each unique nonracemic compound.

In cases in which the platinum compounds have unsaturated carbon-carbon double bonds, both the cis (Z) and trans (E) isomers are within the scope of this invention. In cases wherein the neoplastic compounds may exist in tautomeric forms, such as keto-enol tautomers, such as

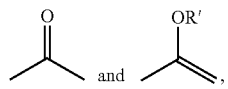

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included as suitable platinum compounds used in the methods of the present invention are prodrugs of the platinum compounds. Prodrugs are considered to be any covalently bonded carriers which release the active parent compound in vivo.

The lipids used in the composition of the aforementioned method can be synthetic, semi-synthetic or naturally-occurring lipids, including phospholipids, tocopherols, sterols, fatty acids, glycolipids, negatively-charged lipids, cationic lipids. In terms of phospholipids, they can include such lipids as egg phosphatidyl choline (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), stearically modified phosphatidylethanolamines, cholesterol derivatives, carotinoids, other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. In particular, the compositions of the compositions can include DPPC, a major constituent of naturally-occurring lung surfactant. Other examples include dimyristoylphosphatidycholine (DMPC) and dimyristoylphosphatidylglycerol (DMPG) dipalmitoylphosphatidcholine (DPPC and dipalmitoylphosphatidylglycerol (DPPG) distearoylphosphatidylcholine (DSPC and distearoylphosphatidylglycerol (DSPG), dioleylphosphatidyl-ethanolamine (DOPE) and mixed phospholipids like palmitoylstearoylphosphatidyl-choline (PSPC) and palmitoylstearolphosphatidylglycerol (PSPG), triacylglycerol, diacylglycerol, seranide, sphingosine, sphingomyelin and single acylated phospholipids like mono-oleoyl-phosphatidylethanolamine (MOPE).

In some embodiments, the lipid complexed active platinum composition comprises a neutral phospholipid, such as a phosphatidyl choline. In other embodiments, the phosphatidyl choline is DPPC.

The cationic lipids used can include ammonium salts of fatty acids, phospholids and glycerides. The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA) and 1,2-bis(oleoyloxy)-3-(trimethylammonio) propane (DOTAP).

Negatively charged lipids include PGs, PAs, PSs and PIs. In some embodiments, the lipid complexed active platinum composition does not comprise a phosphatidyl serine (PS). In some embodiments, the composition does not comprise a PG, PA, PS or PI. In other embodiments, the composition is substantially free of negatively charged or positively charged phospholipids. In some embodiments the composition does not comprise any negatively charged phospholipids.

In some embodiments, the lipid complexed active platinum composition further comprises a sterol. The sterols can include, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. The tocopherols can include tocopherols, esters of tocopherols including tocopherol hemi-succinates, salts of tocopherols including tocopherol hydrogen sulfates and tocopherol sulfates. The term "sterol compound" includes sterols, tocopherols and the like. In some embodiments, the sterol is cholesterol.

In some embodiments, the lipid complexed active platinum composition comprises DPPC and cholesterol in a ratio of about 1:1 to about 5:1 by weight. In other embodiments, composition comprises DPPC and cholesterol in a ratio of about 2:1 to about 4:1 by weight. In some embodiments, the composition comprises DPPC and cholesterol in a ratio of about 2.25:1 by weight.

In some embodiments, the composition further comprises a pharmaceutically acceptable carrier or diluent. The composition may be comprised of an squeous dispersion of the lipid complexed active platinum compound. The composition may contain excipients and salts/buffers to provide the appropriate osmolarity and pH. The pharmaceutical excipient may be a liquid, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient. Suitable excipients include trehalose, raffinose, mannitol, sucrose, leucine, trileucine, and calcium chloride. Examples of other suitable excipients include (1) sugars, such as lactose, and glucose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The present invention, in part, discloses methods of treating cancer more effectively which may have lower nephrotoxicity previously not disclosed. By using lipid-complexed compositions and ip delivery, a more potent and efficient cancer treatment is achieved.

Dosages

The dosage of any compositions of the present invention will vary depending on the symptoms, age and body weight of the patient, the nature and severity of the disorder to be treated or prevented, the route of administration, and the form of the subject composition. Any of the subject compositions may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 50 mg per kg.

Dosage amounts are also commonly administered as $mg/m^2$ which stands for milligrams of drug (e.g. platinum compound) per body surface area. Generally, dosage amounts for platinum compounds may be about 60 $mg/m^2$ or greater, 100 $mg/m^2$ or greater, 140 $mg/m^2$ or greater, or 180 $mg/m^2$ or greater. Dosage amounts of about 140 $mg/m^2$ or greater are generally considered at the high end of tolerance, but an advantage of the present invention is that the platinum compound is administered as part of a lipid-complexed composition which decreases the sub-acute toxicities of the platinum compound. It is therefore envisioned by the inventors that higher than normal dosage amounts of platinum compound may be administered to the patient without unwanted toxic side effects. Higher dosages may lead to longer duration cycles between dosages and greater convenience for the patient. For example, dosage amounts are generally administered to the patient once about every three weeks. If higher dosage amounts of platinum compound can be administered safely to the patient then the cycle time may be increased to once about every four, five, six, seven, or even eight weeks. Longer cycle times means less trips to a care facility for treatment and less times the patient would have to undergo the administration process.

An effective dose or amount, and any possible affects on the timing of administration of the composition, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the antineoplastic compound) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

EXEMPLIFICATION

Example 1

Method of Producing an Aqueous Cisplatin with Higher Potency than its Aqueous Solubility Limit at Room Temperature
1) At temperatures about 50-60° C., cisplatin in 0.9% sodium chloride solution at a level of 4 mg/ml and an ethanolic solution of about 16 mg/ml DPPC and 8 mg/ml cholesterol at about 55° C. are aseptically prepared.

2) The lipid solution is infused into the cisplatin solution while mixing the cisplatin solution.

3) After infusion, cisplatin/lipid dispersion is cooled down to about 10° C. and then warmed up again to about 50-60° C. for 15 min.

4) Step 3) is repeated 2-3 times.

5) The dispersion is aseptically washed with sterile 0.9% sodium chloride solution to remove residual ethanol and un-associated cisplatin via 500,000 MW cut-off membrane diafiltration unit.

After washing process, the dispersion provides about 1 mg/ml cisplatin potency and concentrated to 3 mg/ml cisplatin and further concentrated to 5 mg/ml cisplatin by aseptically removing two third of the aqueous vehicle of 1 mg/ml product and four fifth of the aqueous vehicle of 1 mg/ml product, respectively. The removal of aqueous vehicle was carried out at a rate of about 100 ml/min by diafiltration at about 20° C. without compensating the permeate with fresh sterile 0.9% sodium chloride solution.

Example 2

70 mg DPPC and 28 mg cholesterol was dissolved in 1 mL ethanol and added to 10 mL of 4 mg/mL cisplatin in 0.9% saline solution.

(i) An aliquot (50%) of the sample was treated by 3 cycles of cooling to 4° C. and warming to 50° C. The aliquot, in a test tube, was cooled by refrigeration, and heated in a water bath. The resulting unentrapped cisplatin (free cisplatin) was washed by dialysis.

(ii) The remainder of the sample was not treated by temperature cycles and directly washed by dialysis.

TABLE 1

Percentage entrapment of cisplatin with and without cooling and warming cycles.

| | Final Concentration of cisplatin, μg/mL | % Entrapment |
|---|---|---|
| Lipid-complexed cisplatin without cooling and warming cycles | 56 | 1.4 |
| lipid-complexed cisplatin after cooling and warming cycles | 360 | 9.0 |

Example 3

The rigidity of a membrane bilayer in lipid-complexed cisplatin prepared with cool/warm cycling as described in Example 2 was measured by fluorescence anisotropy of diphenylhexatriene (membrane probe) inserted in the hydrophobic core region of the bilayer. [Ref. Jahnig, F., 1979 *Proc. Natl. Acad. Sci. USA* 76(12): 6361.] The hydration of the bilayers was gauged by the deuterium isotope exchange effect on fluorescence intensity of TMA-DPH (trimethylamine-diphenylhexatriene). [Ref. Ho, C., Slater, S. J., and Stubbs, C. D., 1995 *Biochemistry* 34: 6188.]

TABLE 2

Degree of hydration and rigidity of liposomes, lipid-complexed cisplatin without and with cool/warm cycling.

| | Placebo (Liposomes without cisplatin) | Lipid-complexed cisplatin without cooling & warming cycles | Lipid-complexed cisplatin with cooling & warming cycles |
|---|---|---|---|
| Degree bilayer rigidity | 0.29 | 0.29 | 0.36 |
| Degree of bilayer hydration | 1.13 | 1.15 | 1.02 |

Example 4

Density Characterization of the light and heavy fractions was performed as follows. Samples were prepared as in the previous example. At cooling the temperature of samples was 0° C. The temperature cycle was done by 15 min cooling and 15 min warming. The starting cisplatin concentration was 4 mg/mL and free cisplatin was removed by dialysis.

Density Gradient Analysis

Seven different batches of cisplatin lipid complex were used for these experiments. Density gradients were formed using Iodixanol (SIGMA (D1556, lot no. 025K1414)) as a dense media and 0.9% NaCl saline solution to keep osmolality close to normal 300 mOsM. First, about 5.5 mL saline was added to the centrifuge tube, and then the same volume of heavy medium (1:1 mixture of Iodixanol 60% and saline) was layered on the bottom of the tube using a syringe with a long needle. Gradients were formed using a BioComp 107ip Gradient Master at the settings: time=2:14 min, angle=79.0, speed=17 rpm, and using the long tube cap. An aliquot of Cisplatin Lipid Complex samples (1 mL) were placed on the top of the gradient and centrifuged for 30 min at 30,000 rpm at 20° C. After centrifugation, the top 0.8-1.0 mL volume of clear liquid was discarded, and the next 2 mL was collected representing the light fraction. The light fraction is believed to contain liposomes, wherein at least some of the liposomes are associated with cisplatin. There was a detectable amount of free cisplatin in the light fraction of nebulized samples, which was determined by filtering through Centricon-30 filtering devices and subtracted from the total cisplatin.

The rest of the media was removed, leaving only a small yellow pellet on the bottom representing the dense (heavy) fraction, which was subsequently dispersed in 2 mL solution of 75% n-Propanol, 5% saline, 20% water. Cisplatin in the heavy fraction was not completely soluble at this point. An aliquot of this dispersion was taken for cisplatin determination. Another part of the dispersion (1 mL) was mixed with equal volume of 60% n-Propanol and centrifuged 5 min at 1000 rpm on an Eppendorf 5810R centrifuge to settle undissolved cisplatin, and then 1 mL of clear supernatant was used for HPLC lipid determination.

Cisplatin Concentration:

Cisplatin was measured by HPLC by separating cisplatin on YMC-Pack NH2 column using 90% acetonitrile mobile phase and measuring absorbance at 305 nm. Cisplatin standards and samples were diluted in solution of 75% n-Propanol, 5% saline and 20% water. Standards were used with cisplatin concentrations of 75, 50, 25, and 10 μg/mL. Cisplatin peak retention time was usually around 6.4 min.

Lipid Analysis by HPLC:

Lipids were analyzed by HPLC as follows: lipids were separated on a Phenomenex Luna C8(2) column using binary gradient mode. Mobile phase A: methanol 70%, acetonitrile 20%, water 10%, ammonium acetate 0.1%, mobile phase B: methanol 70%, acetonitrile 30%, ammonium acetate 0.07%. Lipid standards and samples were diluted in a solution of 60% n-Propanol, 40% water. Lipids were detected by Sedex 55 Evaporative Light Scattering Detector. The retention time for cholesterol was about 8 min, for DPPC about 10 min.

Results

Nine batches of Lipid-cisplatin complex were fractionated on an Iodixanol density gradient as described in the Methods section. All nine samples separated into a similarly positioned white band of light fraction and a yellow pellet of dense fraction. 2 mL of the light fraction were collected and the rest of the liquid was removed. The remaining pellet was dispersed in 2 mL of 75% n-Propanol. Cisplatin and lipid concentrations in each fraction were measured by HPLC as described. The lipid/cisplatin ratio in the dense fraction was very high so that both lipid and cisplatin could not be solubilized in same solvent at high enough concentration for the lipid analysis. For that reason, the lipid-cisplatin mixture in 75% n-propanol solution was centrifuged to remove the insoluble portion of the cisplatin, and the supernatant was used as is for lipid HPLC analysis.

Results of the density gradient analysis are presented in Table 4. L/D represents the ratio of lipid to cisplatin by weight. The percentages presented are with respect to the total cisplatin or lipid in the formulation. Lower section of the table shows averages of lipid and cisplatin contents in each fraction derived from all nine samples tested. Standard deviations (SD) are shown to demonstrate consistency. These data demonstrate that the majority of lipid (90.6% on average, +/-3.1%) is in the light fraction, while only 0.87+/-0.09% lipid is in the dense fraction. The majority of cisplatin (82.3+/-2.9%) is in the dense fraction, while only 8.4+/-2.1% is in the light fraction. The lipid to drug ratio (L/D) calculated for the total sample was an average of 22.7. The same L/D ratio in separate fractions was as high as 255+/-47 for the light fraction, and as low as 0.24+/-0.03 for dense fraction. Results are summarized in Table 3.

TABLE 3

Distribution of cisplatin and lipids in the light and dense fractions of Cisplatin Lipid Complex samples.

| Batch | Lipid mg/mL | Lipid % total | Cisplatin mg/mL | Cisplatin % total | L/D |
|---|---|---|---|---|---|
| 8 total | 62.2 | | 2.47 | | 25.2 |
| 8 Light fraction | 58.0 | 93.3 | 0.20 | 8.2 | 285 |
| 8 Dense fraction | 0.49 | 0.79 | 2.01 | 81.3 | 0.24 |
| 9 total | 51.5 | | 2.46 | | 20.9 |
| 9 Light fraction | 47.8 | 92.7 | 0.18 | 7.2 | 270 |
| 9 Dense fraction | 0.44 | 0.85 | 1.96 | 79.7 | 0.22 |
| 10 total | 55.2 | | 2.57 | | 21.5 |
| 10 Light fraction | 46.7 | 84.7 | 0.20 | 7.7 | 237 |
| 10 Dense fraction | 0.47 | 0.85 | 2.15 | 83.6 | 0.22 |
| 11 total | 57.3 | | 2.61 | | 22.0 |
| 11 Light fraction | 49.7 | 86.8 | 0.15 | 5.9 | 326 |
| 11 Dense fraction | 0.48 | 0.84 | 2.20 | 84.2 | 0.22 |
| 12 total | 57.9 | | 2.57 | | 22.5 |
| 12 Light fraction | 51.6 | 89.1 | 0.18 | 6.9 | 290 |
| 12 Dense fraction | 0.47 | 0.82 | 2.17 | 84.3 | 0.22 |
| 13 total | 80.46 | | 3.36 | | 24.0 |
| 13 Light fraction | 73.42 | 91.26 | 0.44 | 13.0 | 168 |
| 13 Dense fraction | 0.82 | 1.01 | 2.58 | 76.7 | 0.32 |
| 14 total | 71.19 | | 3.41 | | 20.9 |
| 14 Light fraction | 64.82 | 91.06 | 0.29 | 8.7 | 220 |
| 14 Dense fraction | 0.65 | 0.92 | 2.76 | 81.1 | 0.24 |
| 15 total | 66.92 | | 2.83 | | 23.7 |
| 15 Light fraction | 62.35 | 93.17 | 0.23 | 8.0 | 275 |
| 15 Dense fraction | 0.66 | 0.99 | 2.45 | 86.5 | 0.27 |
| 16 total | 68.5 | | 2.86 | | 23.9 |
| 16 Light fraction | 64.0 | 93.48 | 0.28 | 9.8 | 228 |
| 16 Dense fraction | 0.51 | 0.75 | 2.40 | 83.8 | 0.21 |
| Average | | | | | 22.7 |
| Light fraction | | 90.6 | | 8.4 | 255 |
| +/-SD | | 3.1 | | 2.1 | 47 |
| Dense fraction | | 0.87 | | 82.3 | 0.24 |
| +/-SD | | 0.09 | | 2.9 | 0.03 |

Example 5

Separation of Light and Dense Fractions 30 mL of cisplatin lipid complex was mixed with 10 mL iodixanol 30% in saline. This mixture was in half and 20 mL portions were layered on the top of another 10 mL iodixanol 30% in saline using two 50 mL centrifuge tubes. The samples were centrifuged for 30 minutes at 4000 rpm at 5° C. on an Eppendorf 5810 centrifuge. Supernatant, containing a mixture of light and heavy fractions, was discarded. The pellet, containing the dense fraction of the cisplatin lipid composition, was gently dispersed in 5 mL of saline. After determining the concentration of cisplatin, the concentration was adjusted to make the concentration 2.7 mg/mL of cisplatin.

To obtain the light fraction, the cisplatin lipid complex batch was allowed to settle by gravity at 5° C. for 1 week. The top portion of the sample, containing the light fraction, was collected.

Example 6

Entrapment of cisplatin or transplatin in a lipid complex by repetitive cooling/heating achieves a high drug/lipid ratio as shown in Table 4.

TABLE 4

| | cisplatin | transplatin |
|---|---|---|
| Starting drug concentration | 5 mg/mL | 1 mg/mL |
| Lipids (DPPC:Cholesterol = 7:3 wt) | 25 mg/mL | 5 mg/mL |
| Temperature cycles | 6 cycles | 6 cycles |
| Final drug concentration | 1.4 mg/mL (1.4% free) | 0.3 mg/mL (6.0% free) |
| Recovery % | 29% | 26% |
| Drug/Lipid | 0.056 | 0.06 |

Example 7

Samples of the heavy fraction comprising lipid-complexed cisplatin were diluted in filtered saline (NaCl 0.9%) at a ratio of 1:2000 and analyzed by an AccuSizer Optical Particle Sizer 780 using the following settings: injection loop volume 1 mL, Data collection time 60 s, Detector LE 400-05SE summary mode, Minimum diameter 0.05 microns. The detector used counts only particles 0.5 microns and larger. Four batches were analyzed. The distribution plots show relative volumes occupied by particles of different sizes. The particles in the range of 0.5 to 1 micron represent the main distribution of the light fraction, the majority of which has particle sizes less than 5 microns. The plots also show a large peak at the right from 1 micron to 20 micron, with a median size of about 8 to 10 microns.

Example 8

Comparison of free cisplatin and lipid-complexed cisplatin formulation at 3 mg/ml cisplatin concentration administered intraperitoneally to rats. Male Sprague-Dawley rats were given free cisplatin at dosages of 6 and 12 mg/kg, and lipid-complexed cisplatin formulations at 3 mg/ml at dosages of 6, 12, and 18 mg/kg intraperitoneally. Control groups comprised 6 rats and groups for the test articles comprised 3 rats per group. Observation of morbidity/mortality were conducted daily as were weight measurements. Results are presented in Table 5.

TABLE 5

Rat study lethality summary for 3 mg/ml lipid-complexed cisplatin formulation.

| Treatment Group/Dosage | Number Dead/Number Treated | Day of Death |
|---|---|---|
| Group 1 - Control (no treatment) | 0/6 | |
| Group 2 - 6 mg/kg lipid-complexed cisplatin formulation | 0/3 | |
| Group 3 - 12 mg/kg lipid-complexed cisplatin formulation | 1/3 | 13 |
| Group 4 - 18 mg/kg lipid-complexed cisplatin formulation | 1/3 | 8 |

Example 9

Reduction of sub-acute toxicity of cisplatin by iv or ip administration when administered as a lipid-complexed formulation. ICR mice, male and female, 6-7 weeks old, were divided into 24 groups with 10 mice in each. Five mice were housed in each cage with free access to standard mouse food and water. Each group of mice was injected with lipid-complexed cisplatin formulations prepared according to the following. The lipid-complexed cisplatin formulation used here contained 1 mg/ml cisplatin, 16 mg/ml DPPC, and 7.9 mg/ml cholesterol in 0.9% NaCl solution. An aliquot (50%) of the sample was treated by 3 cycles of cooling to 4° C. and warming to 50° C. The aliquot, in a test tube, was cooled by refrigeration, and heated in a water bath. The resulting unentrapped cisplatin (free cisplatin) was washed away by dialysis. The lipid-complexed cisplatin in the form of liposomes were injected through iv (tail vein) or ip route. The liposomes had a mean diameter of about 0.39 μm. The formulations, doses, and administration routes are listed in Table 6.

TABLE 6

Dose and administration route for lipid-complexed cisplatin sub-acute toxicity study.

| Formulation | Route | Dose (mg Cisplatin/kg mouse) | | | | | | |
|---|---|---|---|---|---|---|---|---|
| Lipid-Complexed Cisplatin | ip | 23 | 27 | 31 | 35 | 40 | 45 | 50 |
| Cisplatin | ip | 9 | 12 | 15 | 18 | 21 | 24 | 27 |

Starting one week before the administration, body weights of the mice were measured every two days until the end of the experiment. The animals were observed daily and the death was recorded. A curve of percent survival verses time (days) post administration for each formulation with each injection route was calculated (FIG. 1). The $LD_{10}$, $LD_{50}$ and $LD_{90}$ of each formulation under each injection route were estimated. The computer fitted results are listed in Table 7.

TABLE 7

Lethal toxicity of lipid-complexed cisplatin and cisplatin after ip and iv injection.

| Formulation | Route | Lethal Dose (mg Cisplatin/kg mouse) | | |
|---|---|---|---|---|
| | | $LD_{10}$ | $LD_{50}$ | $LD_{90}$ |
| Lipid-Complexed Cisplatin | ip | 22.4 | 29.5 | 38.9 |
| Cisplatin | ip | 9.9 | 14.3 | 20.7 |

The result indicate that the sub-acute toxicity of ip lipid-complexed cisplatin was 2-fold lower than ip cisplatin, whereas not nearly as great of change was observed for iv lipid-complexed cisplatin.

Example 10

Pharmacokinetics and organ distribution in animals of ip and iv injected lipid-complexed cisplatin and cisplatin (Part I). The mice (the same as from Example 2) were divided into 4 groups with 24 mice in each. They were injected with ip lipid-complexed cisplatin (12 mg/kg), ip cisplatin (12 mg/kg), iv lipid-complexed cisplatin (8 mg/kg), and iv cisplatin (8 mg/kg), separately. The lipid-complexed cisplatin formulation were prepared in the same manner as in Example 3. At each designed time point, e.g., 2-5 min, 20 min, 40 min, 2 h, 8 h, 1 day, 2 days, and 3 or 5 days after injection, 3 mice from each group were anesthetized by ip injection of 35-50 mg/kg of Nembutal, then the blood was drown and heart, kidney, liver, lung, small intestine, and spleen were resected and homogenized after adding 4-fold pure water. The Platinum concentration in each sample was determined with AA method. The content of Pt (μg of Pt in 1 ml of blood or 1 gram of tissue) was calculated and used for presenting the kinetic characteristics of each formulation under two different administration routes.

Figure 2:
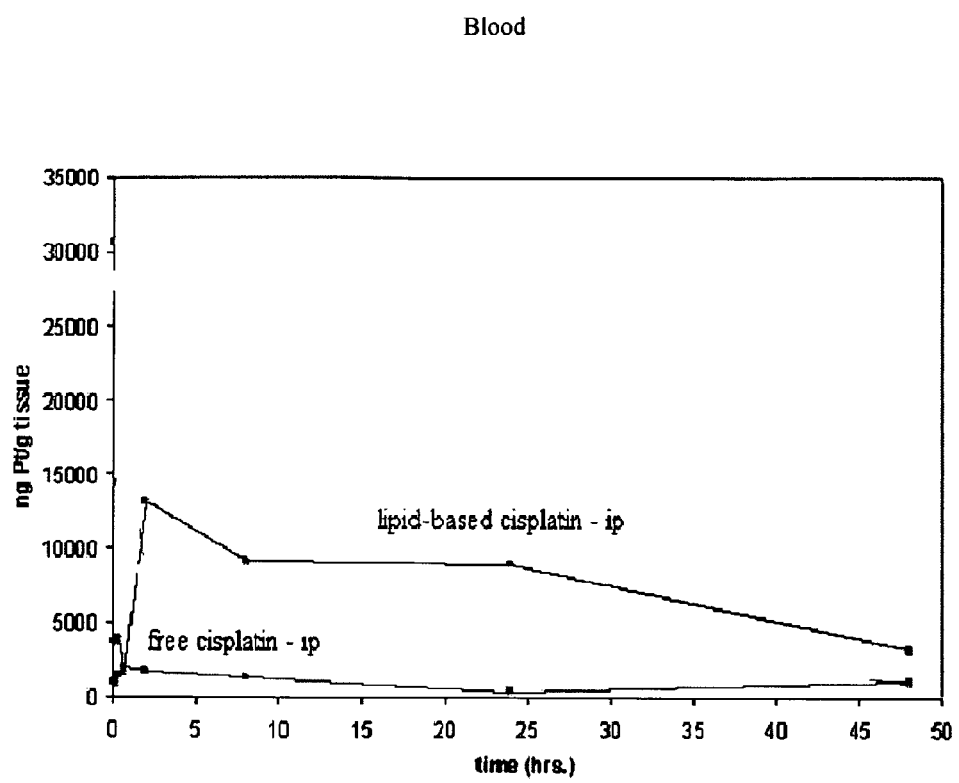
FIG. 2 depicts the increased amount of cisplatin from lipid-complexed cisplatin in the blood stream when administered intraperitoneally as compared to free cisplatin administered intraperitoneally.
Figure 3:
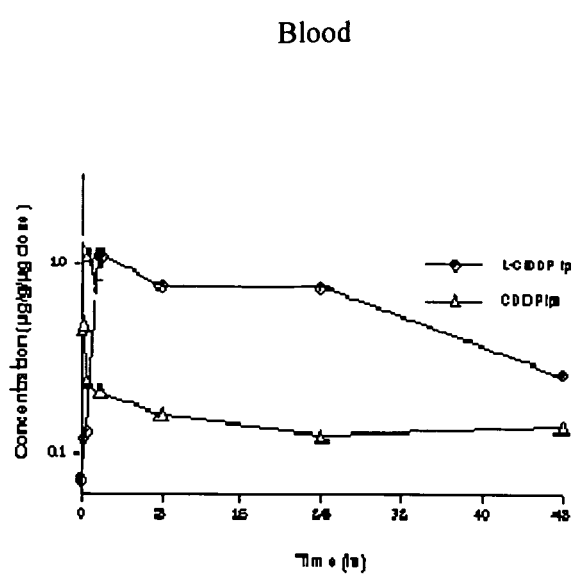
FIG. 3 depicts the increased amount of cisplatin in the blood stream from lipid-complexed cisplatin when administered intraperitoneally as compared to free cisplatin administered intraperitoneally.
Figure 4:
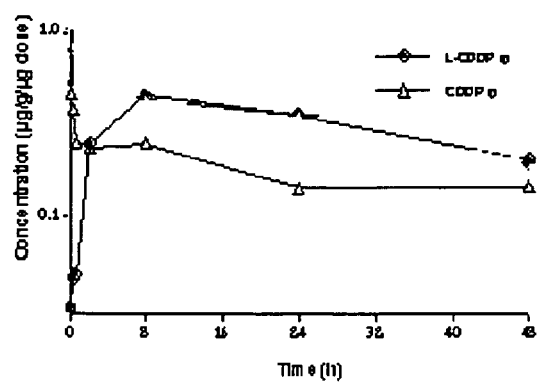
FIG. 4 depicts the increased amount of cisplatin from lipid-complexed cisplatin in the kidney as compared to free cisplatin.
Figure 5:
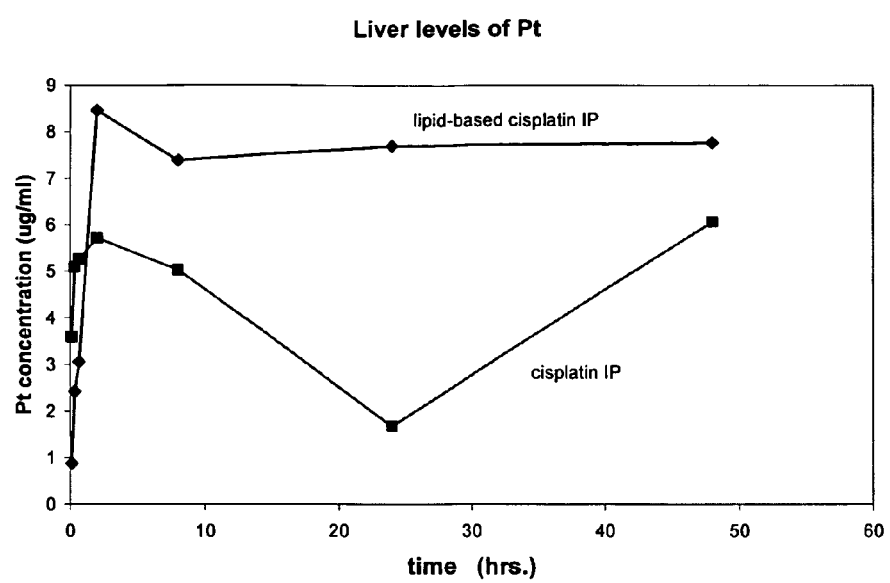
FIG. 5 depicts the higher amount of cisplatin from lipid-complexed cisplatin in the liver as compared to free cisplatin when administered intraperitoneally.
Figure 6:
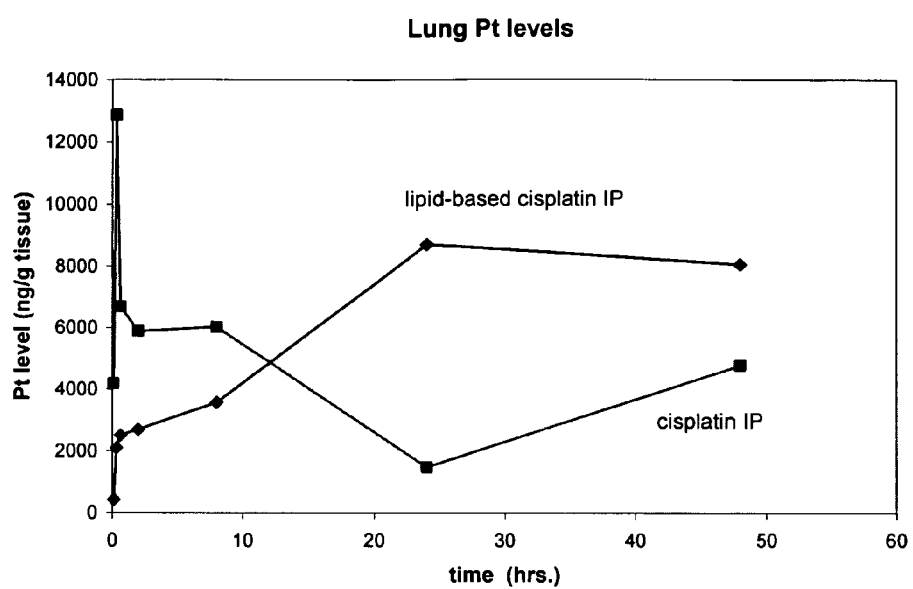
FIG. 6 depicts the higher amount of cisplatin from lipid-complexed cisplatin in the lung as compared to free cisplatin when administered intraperitoneally.
Figure 7:
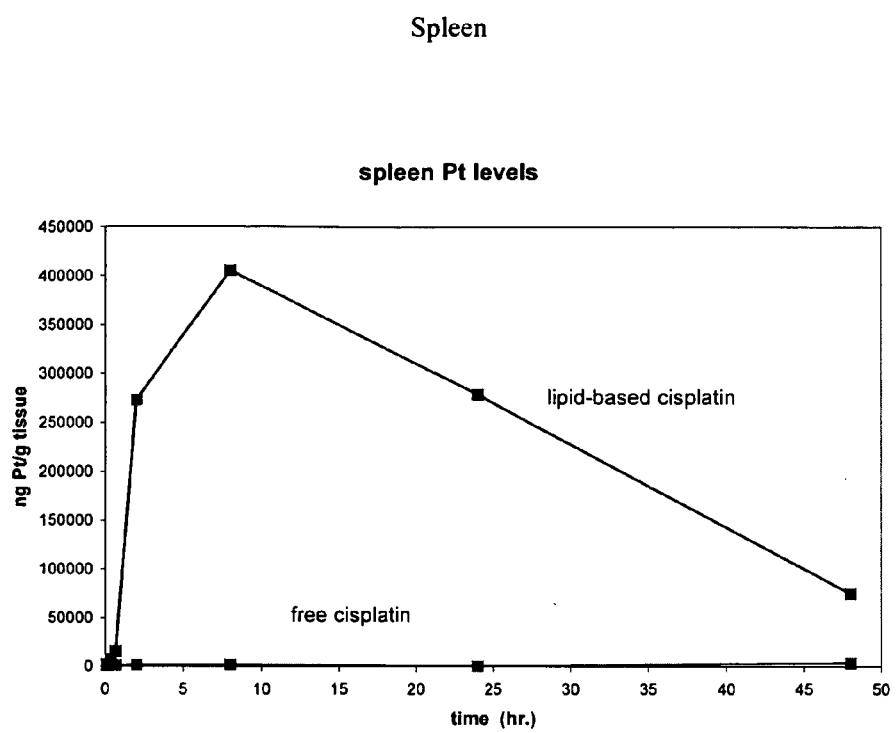
FIG. 7 depicts the increased amount of cisplatin from lipid-complexed cisplatin in the spleen when administered intraperitoneally as compared to free cisplatin administered intraperitoneally.
Figure 8:
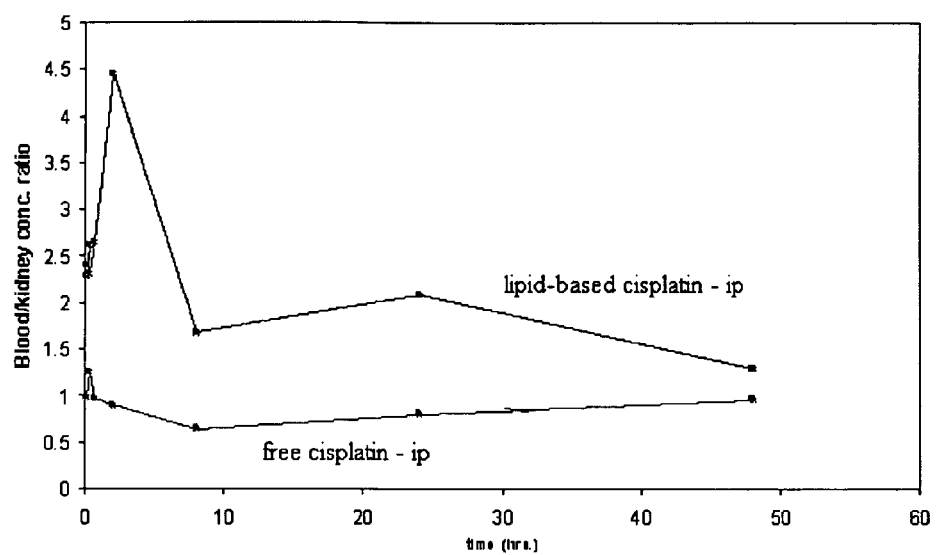
FIG. 8 depicts the blood/kidney concentration ratio of platinum from lipid-complexed cisplatin administered intraperitoneally and free cisplatin administered intraperitoneally.

The results indicated that in the blood, the Cmax and AUC of lipid-complexed cisplatin was 3- and 6-fold higher than that of cisplatin, respectively (FIG. 2).

Example 11

Pharmacokinetics and organ distribution in animals of ip and iv injected lipid-complexed cisplatin and cisplatin (Part II). Sixty ICR mice (female, 7 weeks old) were divided into 4 groups. They received intraperitoneal or intravenous injection of L-CDDP or CDDP, separately. The lipid-complexed cisplatin formulation were prepared in the same manner as in Example 3. The dose was 12 mg/kg for ip L-CDDP and 8 mg/kg for the rest of treatment groups. At each designed time point, three to four mice were anaesthetized with 70 mg/kg of Nembutal ip (e.g., 3, 20, and 40 min, and 2, 8, 24, 48, and 72 h). The blood was drawn from the inferior vena cava. Organs including duodenum, kidney, liver, lung, and spleen were resected from the mice. The blood and organ samples were homogenized in distilled water (4-fold of the sample weight) and digested with nitric acid. The platinum concentration in each sample was measured by Inductively Coupled Plasma-Mass Spectrometer (ICP-MS). The pharmacokinetics profiles (FIGS. 3-7, all Y-axes are concentration of μg platinum in one gram of tissue or fluid per mg of injected dose) and parameters (Tables 4 and 5) of each formulation were simulated and calculated. It was found that 1) uptake of platinum in the spleen was significantly enhanced by the liposomal formulation irrespective of the injection routes, the AUCs and $C_{max}$ were 26~47-fold higher than those of CDDP, p<0.0003; 2) with ip injection, the circulation AUC and elimination $t_{1/2}$ of L-CDDP were 4- and 15-fold (p<0.006) higher than those of CDDP, but this phenomenon was not found after iv injection; 3) the AUC and $t_{1/2}$ of ip L-CDDP were also higher than those of iv L-CDDP (ip vs iv: AUC, 1.9-fold, p=0.04; $t_{1/2}$, 5.7-fold, p=0.006); 4) the lung and liver platinum uptake of iv L-CDDP were slightly higher than that of iv CDDP (Lung: p=0.043; Liver: p=0.051); 5) the kidney platinum uptake of L-CDDP was higher than that of CDDP (p=0.046). These results imply that the formulation and administration route both play important role on the PK and organ distribution of the drug, and ip L-CDDP showed sustained release function.

TABLE 8

Circulation AUC and $t_{1/2}$.

|  | AUC (h μg/g/μg) ip | $t_{1/2}$ (h) ip |
|---|---|---|
| L-CDDP | 37.60[a] | 26.58[b] |
| CDDP | 7.08 | 1.82 |

[a]p = 0.008 (L-CDDP vs CDDP);
[b]p = 0.006 (L-CDDP vs CDDP) by two side Log rank test.

TABLE 9

Organ AUC and $C_{max}$.

| | ip | | | |
|---|---|---|---|---|
| | AUC (h μg/g/μg) | | $C_{max}$ (μg/g/μg) | |
| | L-CDDP | CDDP | L-CDDP | CDDP |
| Duodenum | 5.49 | 8.32 | 0.30 | 0.45 |
| Kidney | 15.60[c] | 8.61 | 0.46 | 0.46 |
| Liver | 29.99 | 28.99 | 0.71 | 0.71 |
| Lung | 26.90 | 29.00 | 0.73 | 1.61 |
| Spleen | 331.86[e] | 10.45 | 11.32[f] | 0.43 |
| Heart | 2.63 | 2.67 | 0.07 | 0.18 |

Two side Log rank test was used to evaluate the significance of the differences of L-CDDP versus CDDP in AUC or $C_{max}$ values. Statistically significant pairs (p < 0.05) were labeled with a superscript letter. Their p values are as follows:
[c]p = 0.046;
[d]p = 0.008;
[e]p = 0.0002;
[f]p = 0.0001;
[g]p = 0.0003;
[h]p = 0.0002.

Example 12

Nephrotoxicity. ICR mice, 7 weeks old, female, were divided into 4 groups with 3 to 4 mice in each. They were injected with maximum tolerated dose (MTD) of L-CDDP or CDDP via iv or ip. The lipid-complexed cisplatin formulation were prepared in the same manner as in Example 3. Four days after the injection, the mice were euthanized with Nembutal ip. The blood was drawn and the serum was isolated. The blood urea nitrogen (BUN) was quantitatively measured with a calorimetric method at Antech Diagnostics. Organs including duodenum, heart, kidney, liver, lung, and spleen were resected from the mice and fixed with 10% buffered Formalin. The fixed tissues were processed with standard procedure for H and E staining. A pathology expert Dr. Carman Tornos at the Memorial Sloan-Kettering Cancer Center examined kidney tissues and gave a toxicity grade to each kidney tissue sample. The grading was based on the general pathology guidelines for kidney toxicity.

Figure 9:
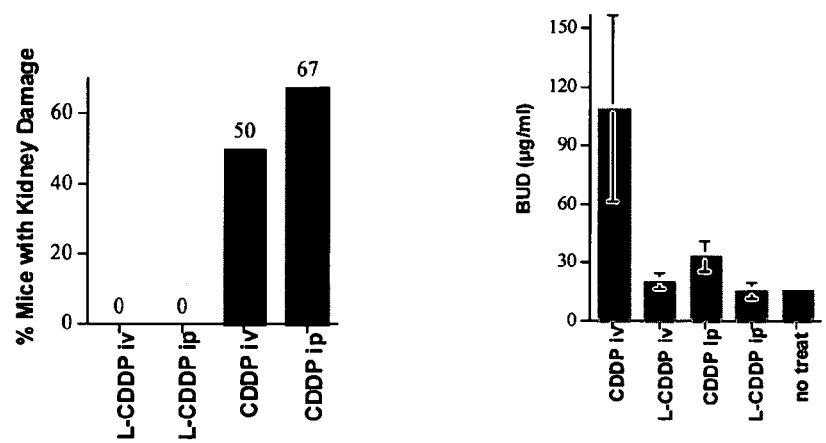
FIG. 9 depicts the increase in blood urea nitrogen (BUN) levels when free cisplatin is delivered either intravenously or intraperitoneally compared to lipid-complexed cisplatin administered by either method.

The pathological results demonstrate that irrespective of administration routes, CDDP caused severe nephrotoxicity in more than 50% mice receiving the treatment, but L-CDDP did not cause any nephrotoxicity. The similar conclusion can be drawn from BUN test (FIG. 9), where iv CDDP significantly increased BUN level by 6.8-fold compared with normal controls (p=0.008), and ip CDDP caused much less BUN accumulation, only 2.1-fold increase compared to normal controls (p=0.04), but L-CDDP injected by either route did not cause BUN level elevation.

Example 13

Preclinical in vivo antitumor activity of lipid-complexed cisplatin in a Murine L1210 tumor model. The purpose of this experiment is to assess the in vivo antitumor activity of lipid-complexed cisplatin against a cavity confined tumor (ascitic L1210 leukemia) by local ip administration. Lipid-complexed cisplatin was compared to free cisplatin for viable L1210 tumor cells. The test articles and materials are presented below in Table 6. The lipid-complexed cisplatin was prepared in the same manner as in Example 3.

TABLE 10

Test articles and materials.

| Test Articles | Cisplatin in 0.9% saline |
| | 1.0 mg/ml cisplatin |
| | Lipid-Complexed Cisplatin |
| | 0.82 mg/ml cisplatin |
| Test Animals | B6D2F1/Hsd hybrid mice from Harlan |
| | 5 male/group except control (9 male), 7 groups |
| Tumor Cells | Viable L1210 tumor cells, |
| | One million per mouse, transplanted in vivo |

The procedure was as outlined below and summarized in Table 11:

1. Day 0, inoculate 6 groups of 5 male mice and 1 group of 9 male control animals with one million viable L1210 cells per mouse by ip injection.

2. Administer ascending doses of either cisplatin solution or lipid-complexed cisplatin to groups of 5 animals. Cisplatin solution: dose ip at 3.0 and 4.5 mg/Kg on days 3, 7, and 11. Each dose level represents one group of five mice. Lipid-complexed cisplatin: dose ip at 3.0, 4.5, 6.0 and 9.0 mg/Kg on days 3, 7, and 11. Control group contains 9 untreated mice.

3. Mice were monitored daily for deaths and or signs of clinical illness. The date of euthanasia was recorded for the purpose of experimental end-points. A total of 39 mice divided into 7 groups were studied. At the end point survival was assessed and expressed as % T/C (percent median survival of treated group: median survival of control group.)

TABLE 11

Procedural parameters

| Group | Mice | Drug tested | ip Dose | Day 0 | Day 3 | Day 7 | Day 11 |
|---|---|---|---|---|---|---|---|
| 1 | 9 male | no treatment | control | inoculate | | | |
| 2 | 5 male | free cisplatin | 3 mg/kg | inoculate | 1 mg/kg | 1 mg/kg | 1 mg/kg |
| 3 | 5 male | free cisplatin | 4.5 mg/kg | inoculate | 1.5 mg/kg | 1.5 mg/kg | 1.5 mg/kg |
| 4 | 5 male | Lipid-complexed cisplatin | 3 mg/kg | inoculate | 1 mg/kg | 1 mg/kg | 1 mg/kg |
| 5 | 5 male | Lipid-complexed cisplatin | 4.5 mg/kg | inoculate | 1.5 mg/kg | 1.5 mg/kg | 1.5 mg/kg |
| 6 | 5 male | Lipid-complexed cisplatin | 6 mg/kg | inoculate | 2 mg/kg | 2 mg/kg | 2 mg/kg |
| 7 | 5 male | Lipid-complexed cisplatin | 9 mg/kg | inoculate | 3 mg/kg | 3 mg/kg | 3 mg/kg |

The results from the experiment are summarized in Table 12.

TABLE 12

Survival data as measured by % T/C.

| Group | Drug tested | Dose | Median survival* | % T/C |
|---|---|---|---|---|
| 1 | no treatment | Control | 13.5 | 100 |
| 2 | free cisplatin | 3 mg/kg | 26.5 | 196 |
| 3 | free cisplatin | 4.5 mg/kg | 29.5 | 218 |
| 4 | Lipid-complexed cisplatin | 3 mg/kg | 19.5 | 144 |
| 5 | Lipid-complexed cisplatin | 4.5 mg/kg | 23.5 | 174 |
| 6 | Lipid-complexed cisplatin | 6 mg/kg | 25.5 | 189 |
| 7 | Lipid-complexed cisplatin | 9 mg/kg | 25.5 | 189 |

*Median survival is defined as day of death for 50% of mice with each group.

Day of death for 50% of mice within each group was determined and an initial % Treated/Control (T/C) value was recorded in the above table. At the optimal dose, the cisplatin in lipid-complexed cisplatin does not lose any of its antitumor activity compared to free cisplatin.

Example 14

Figure 10:
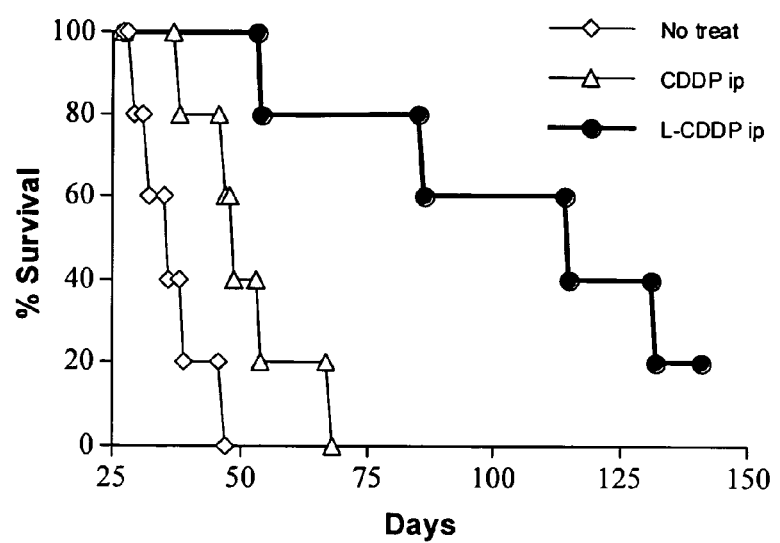
FIG. 10 depicts the survival rate for mice with implanted viable human ovarian cancer cells line SK-OV$_3$-ipl after ip administration of free cisplatin and lipid-complexed cisplatin.

Antitumor activity of L-CDDP against human ovarian cancer xenograft. Nude mice, female, 6-7 weeks old, were intraperitoneally inoculated with human ovarian cancer cell line SK-OV$_3$-ip1 ($1.5 \times 10^6$ cells/mouse). One week after the inoculation, the mice were randomly divided into 3 groups with 5 mice in each. One group of mice was given single bolus ip injection of CDDP with MTD (9 mg/kg) to mimic the current chemotherapy (positive control). Another group was treated with single bolus ip injection of L-CDDP with MTD (23 mg/kg). The lipid-complexed cisplatin formulation were prepared in the same manner as in Example 3. The third group of mice without treatment was used as negative control. The mice were observed on a daily basis. Death of mice was recorded and the increased lifespan (ILS) was calculated. Results are presented in FIG. 10.

Example 15

Comparison of lipid-complexed cisplatin prepared by the cyclic temperature effusion process and non cyclic temperature cisplatin liposomes. The lipid-complexed cisplatin prepared by the cyclic temperature effusion process were prepared as in Example 3 and contained 1.1 mg/ml cisplatin and 27 mg/ml total lipid. The non cyclic temperature cisplatin liposomes were prepared according to the following procedure.

1. DPPC (3.0 g) and cholesterol (1.2 g) were co-dissolved in 20 mL of ethanol.
2. Cisplatin (200 mg) was dissolved in 0.9% saline (200 ml).
3. The lipid/ethanol solution was infused into the cisplatin solution as it was being well-stirred (liposomes formed).
4. The lipid-cisplatin suspension was dialyzed to wash away un-entrapped cisplatin.
5. The resulting liposomal cisplatin contained 0.03 mg/ml total cisplatin (75% of total cisplatin was entrapped and 25% was un-entrapped); the total lipid concentration was 21 mg/ml.

The mice were given equivalent amounts of cisplatin containing therapeutics based on the amount of lipid instead of the amount of cisplatin. This was necessary because in non cyclic temperature cisplatin liposomes the lipid to cisplatin ratio is so high that it is not possible to administer that much lipid necessary to equal the amount of cisplatin in the lipid-complexed formulations prepared as in Example 3.

Female DBA/2 mice (Charles Rivers) were used. Thirty (30) mice were injected with $2 \times 10^6$ L1210 cells ip on Day 0. On day 1, the mice were weighed and randomized into 3 groups of 10 mice. On days 5, mice received a single bolus intraperitoneal injection of soluble cisplatin (6 mg/kg), lipid-complexed cisplatin (6 mg/kg, ip) or non cyclic temperature cisplatin liposomes (equal lipid to lipid-complexed cisplatin, 0.2 mg/kg). Survival was monitored. Mice were weighed daily after day 10. Mice that lost 20% or greater of their starting weight were euthanized by $CO_2$ inhalation. The date of their death was recorded on data sheets. Median survival was calculated by Prism GraphPad.

Figure 11:
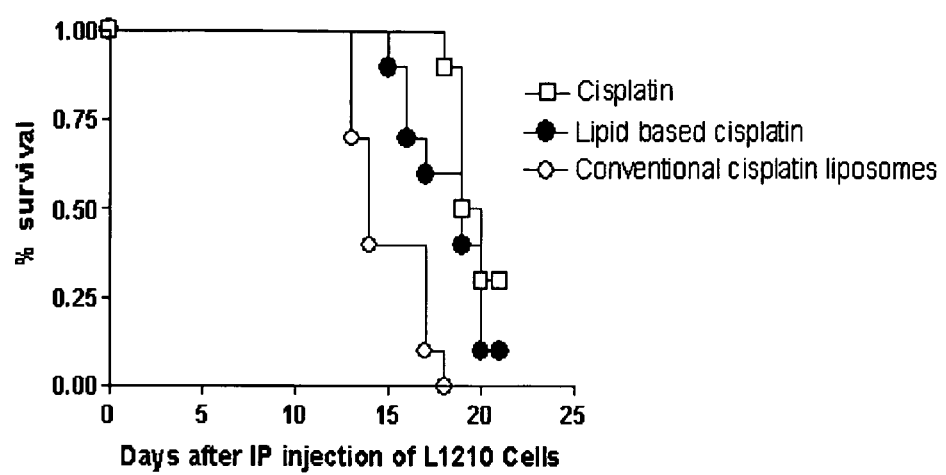
FIG. 11 depicts the survival rate for mice with implanted viable L1210 tumor cells after ip administration of lipid-complexed cisplatin, non-cyclic temperature cisplatin liposomes, and soluble cisplatin.

The results of experiments where both types of cisplatin formulations were administered intraperitoneally to mice with implanted viable L1210 tumor cells are depicted in FIG. 11. There was no significant difference between survival curves of mice that received lipid-complexed cisplatin intraperitoneally and those that received soluble cisplatin intraperitoneally (p=0.20). All survival curves of cisplatin-treated groups were significantly different from the mice that received non cyclic temperature cisplatin liposomes (p=0.0035, and p<0.0001, respectively). The days of median survival were 19 for lipid-complexed cisplatin, ip; 19.5 for free cisplatin, ip; and 14 for non cyclic temperature cisplatin liposomes, ip.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treating a cancer, comprising administering intraperitoneally to a patient in need thereof a composition comprising a therapeutic amount of a lipid-complexed active platinum compound aggregate, wherein the lipid component of the lipid-complexed active platinum compound aggregate consists of electrically neutral lipids; and the lipid to active platinum compound weight ratio (L/D) in the lipid-complexed active platinum compound aggregate is from about 0.10 (L/D) to about 0.50 (L/D).

2. The method of claim 1, wherein the lipid to active platinum compound weight ratio is from about 0.15 (L/D) to about 0.45 (L/D).

3. The method of claim 2, wherein the lipid to active platinum compound weight ratio is from about 0.20 (L/D) to about 0.40 (L/D).

4. The method of claim 3, wherein the lipid to active platinum compound weight ratio is about 0.2 (L/D).

5. The method of claim 1, wherein the lipid-complexed active platinum compound aggregate has an average volume-weighted diameter of about 0.5 to about 20 microns.

6. The method of claim 5, wherein the average volume-weighted diameter of the lipid-complexed active platinum compound aggregate is about 1 to about 15 microns.

7. The method of claim 5, wherein the average volume-weighted diameter of the lipid-complexed active platinum compound aggregate is about 2 to 10 microns.

8. The method of claim 1, wherein the therapeutic amount of the active platinum compound aggregate in the composition ranges from about 1.2 mg/ml to about 20 mg/ml.

9. The method of claim 8, wherein the therapeutic amount of the active platinum compound aggregate ranges from about 1.5 to about 5 mg/ml.

10. The method of claim 1, wherein the lipid-complexed active platinum compound contains about 70% to about 100% of total active platinum compound in the composition.

11. The method of claim 10, wherein the lipid-complexed active platinum compound contains about 75% to about 99% of the total active platinum compound in the composition.

12. The method of claim 11, wherein the lipid-complexed active platinum compound contains about 80% to about 90% of the total active platinum compound in the composition.

13. The method of claim 1, wherein the lipid-complexed active platinum compound contains about 0.1% to about 5% of total lipid in the composition.

14. The method of claim 13, wherein lipid-complexed active platinum compound contains about 0.25% to about 3% of the total lipid in the composition.

15. The method of claim 1, wherein the active platinum compound is selected from the group consisting of cisplatin, carboplatin (diammine(1,1-cyclobutanedicarboxylato)-platinum(II)), tetraplatin (ormaplatin) (tetrachloro (1,2-cyclohexanediamine-N,N')-platinum(IV)), thioplatin (bis(0-ethyldithiocarbonato)platinum(II)), satraplatin, nedaplatin, oxaliplatin, heptaplatin, iproplatin, transplatin, lobaplatin, cis aminedichloro(2-methylpyridine) platinum, JM118 (cis-amminedichloro(cyclohexylamine) platinum(II)), JM 149 (cis-amminedichloro(cyclohexylamine)-trans-dihydroxoplatinum(IV)), JM216 (bis-acetato-cis-amminedichloro (cyclohexylamine) platinum(IV)), JM335 (trans-amminedichloro (cyclohexylamine)dihydroxoplatinum (IV)), (trans, trans, trans)bis-mu-(hexane-1,6-diamine)-mu-[diamine-platinum(II)]bis[diamine(chloro) platinum(II)] tetrachloride, and a mixture thereof.

16. The method of claim 1, wherein the active platinum compound is cisplatin.

17. The method of claim 1, wherein the electrically neutral lipids consist of a phosphatidylcholine.

18. The method of claim 17, wherein the phosphatidylcholine is dipalmitoylphosphatidylcholine (DPPC).

19. The method of claim 1, wherein the electrically neutral lipids consist of dipalmitoylphosphatidylcholine (DPPC) and a sterol.

20. The method of claim 19, wherein the sterol is cholesterol.

21. The method of claim 20, wherein the electrically neutral lipids consist of dipalmitoylphosphatidylcholine (DPPC) and cholesterol in a ratio of about 1:1 by weight to about 5:1 by weight.

22. The method of claim 21, wherein the electrically neutral lipids consist of dipalmitoylphosphatidylcholine (DPPC) and cholesterol in a ratio of about 2:1 by weight to about 4:1 by weight.

23. The method of claim 22, wherein the electrically neutral lipids consist of dipalmitoylphosphatidylcholine (DPPC) and cholesterol in a ratio of about 2.25:1 by weight.

24. The method of claim 1, wherein the cancer is selected from the group consisting of melanoma, testis (germ cell) cancer, osteosarcoma, soft tissue sarcoma, thyroid cancer, colon cancer, ovarian cancer, cancer of the kidney, breast cancer, colorectal cancer, prostate cancer, bladder cancer, uterine cancer, lung cancer, stomach cancer, liver cancer, spleen cancer, endometrial, and squamous cell carcinomas of the head and neck.

25. The method of claim 1, wherein the cancer is ovarian cancer.

26. The method of claim 1, wherein the patient is a human.

27. The method of claim 1, wherein the composition is administered to the patient at least once every three weeks.

28. The method of claim 1, wherein the therapeutic amount of the active platinum compound aggregate in the composition is at least 60 milligrams per body surface area (mg/m$^2$).

29. The method of claim 1, wherein the therapeutic amount of the active platinum compound aggregate in the composition is at least 100 milligrams per body surface area (mg/m$^2$), and the composition is administered to the patient at least once every three weeks.

30. The method according to claim 1, wherein the therapeutic amount of the active platinum compound aggregate in the composition is at least 140 milligrams per body surface area (mg/m$^2$).

31. The method of claim 1, wherein the therapeutic amount of the active platinum compound aggregate in the composition is at least 180 milligrams per body surface area (mg/m$^2$).

* * * * *